US011628216B2

(12) United States Patent
Banaszczyk et al.

(10) Patent No.: US 11,628,216 B2
(45) Date of Patent: *Apr. 18, 2023

(54) 6-ACETYLMORPHINE ANALOGS, AND METHODS FOR THEIR SYNTHESIS AND USE

(71) Applicant: ALERE SAN DIEGO, INC., San Diego, CA (US)

(72) Inventors: Mariusz Banaszczyk, San Marcos, CA (US); Normand Hébert, Encinitas, CA (US); Neil Stowe, San Diego, CA (US)

(73) Assignee: ALERE SAN DIEGO, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/536,718

(22) Filed: Nov. 29, 2021

(65) Prior Publication Data
US 2022/0080042 A1 Mar. 17, 2022

Related U.S. Application Data

(60) Continuation of application No. 16/105,299, filed on Aug. 20, 2018, now abandoned, which is a division of application No. 15/640,781, filed on Jul. 3, 2017, now Pat. No. 10,052,379, which is a division of application No. 14/775,644, filed as application No. PCT/US2014/027585 on Mar. 14, 2014, now Pat. No. 9,694,069.

(60) Provisional application No. 61/952,719, filed on Mar. 13, 2014, provisional application No. 61/785,538, filed on Mar. 14, 2013.

(51) Int. Cl.
| A61K 39/385 | (2006.01) |
| C07D 489/02 | (2006.01) |
| C07D 489/00 | (2006.01) |
| C07D 489/04 | (2006.01) |
| C07F 9/6561 | (2006.01) |
| A61K 39/00 | (2006.01) |
| A61K 39/39 | (2006.01) |
| C07K 16/06 | (2006.01) |
| C07K 16/44 | (2006.01) |
| C08L 25/06 | (2006.01) |
| G01N 33/94 | (2006.01) |

(52) U.S. Cl.
CPC ........ *A61K 39/385* (2013.01); *A61K 39/0013* (2013.01); *A61K 39/39* (2013.01); *C07D 489/00* (2013.01); *C07D 489/02* (2013.01); *C07D 489/04* (2013.01); *C07F 9/6561* (2013.01); *C07K 16/06* (2013.01); *C07K 16/44* (2013.01); *C08L 25/06* (2013.01); *G01N 33/9486* (2013.01); *A61K 2039/6081* (2013.01); *A61K 2039/627* (2013.01); *C07K 2317/33* (2013.01)

(58) Field of Classification Search
CPC ...... A61K 2039/6081; A61K 2039/627; A61K 39/0013; A61K 39/385; A61K 39/39; C07D 489/00; C07D 489/02; C07D 489/04; C07F 9/6561; C07K 16/06; C07K 16/44; C07K 2317/33; C08L 25/06; G01N 33/9486
See application file for complete search history.

(56) References Cited

U.S. PATENT DOCUMENTS

| 5,610,283 A | 11/1997 | Buechler et al. |
| 6,262,265 B1 | 7/2001 | Rouhani et al. |
| 2007/0142628 A1 | 6/2007 | Ghoshal et al. |

FOREIGN PATENT DOCUMENTS

| WO | WO 98014216 | 4/1998 |
| WO | WO 2011041470 | 4/2011 |
| WO | WO 2012139015 | 10/2012 |
| WO | WO 2013095321 | 6/2013 |
| WO | WO 2013119954 | 8/2013 |

OTHER PUBLICATIONS

Alnajjar and El-Zaria, Synthesis and characterization of novel azo-morphine derivatives for possible use in abused drugs analysis, Eur J Med Chem. Feb. 2008;43(2):357-363.
Bremer et al., Investigating the Effects of a Hydrolytically Stable Hapten and a Th1 Adjuvant on Heroin Vaccine Perfomance. J Med Chem. Dec. 13, 2012;55(23):10776-10780.
Exam Report issued by IP Australian in Australian patent application No. 2014239248 dated Mar. 21, 2016.
International Search Report and Written Opinion dated Jul. 14, 2014 in PCT/US2014/027585 (8 pages).
Second Examination Report issued in Australian patent application No. 2014239248 dated Aug. 19, 2016.
Genady, Synthesis and Characterization of Novel Color Chemosensors Based on Azo Dyes for Possible Application in Opioid Pharmacology. J Heterocyclic Chem. 2010;47:1134-1143.
Houdi et al., 3-O-Acetylmorphine-6-O-sulfate: A potent, centrally acting morphine derivative. Pharmacol Biochem Behav. Mar. 1996;53(3):665-671.
Small and Mallonee, Acetomorphine and Acetocodeine. J Org Chem. Jul. 1947;12(4):558-566.
Small, L. et al. J. Org. Chem 1947, vol. 12, pp. 558-566.
Stowe, G. N. et al., J. Med. Chem. 2011 vol. 54, pp. 5195-5204.

(Continued)

Primary Examiner — Galina M. Yakovleva
(74) Attorney, Agent, or Firm — Casimir Jones, S.C.; Anne M. Reynolds

(57) ABSTRACT

The present invention relates to novel 6-acetylmorphine analogs, and methods for their synthesis and use. Such analogs are designed to provide a convenient linkage chemistry for coupling under mild conditions to a suitable group on a target protein, polypeptide, solid phase or detectable label.

15 Claims, 11 Drawing Sheets

(56) References Cited

OTHER PUBLICATIONS

Goodrow et al. Strategies for Immunoassay liapten Design. Immunoanalysis of Agrochemicals; Nelson, J. et al. ACS Symposium Series, 1995, vol. 586, Chapter 9, 119-139.

Szurdoki et al. Important Factors in Hapten Design and Enzyme-Linked Immunosorbent Assay Development. Immunoanalysis of Agrochemicals, Nelson, J. et al.; ACS Symposium Series, 1995, vol. 586, Chapter 4, 39-63.

Lloyd et al. Modelling the human immune response: performance of a 1011 human antibody repertoire against a broad panel of therapeutically relevant antigens. Protein Eng Des Sel. Mar. 2009;22(3):159-68.

A printout retreived from http://www.qcbio.com/pierce/77605.htm on Jan. 28, 2021.

6-Phosphinyl Alkane

6-Phosphinyl Alkene

6-Alkyl Alkane
n = 0, 1

6-Alkyl Alkene
n = 0, 1

1-Aminopropenyl-N-Bromoacetyl-6PM

1-Aminopropenyl-N-Bromoacety-6-AHM

1-Aminopropyl-N-Bromoacetyl-6PM

1-Aminopropyl-N-Bromoacety-6-AHM

1-Maleimido-N-propyl-6PM

1-Maleimido-N-ypropyl-6-AHM

1-Maleimido-N-propenyl-6PM

1-Maleimido-N-propenyl-6-AHM

6-ACETYLMORPHINE ANALOGS, AND METHODS FOR THEIR SYNTHESIS AND USE

CROSS-REFERENCE TO RELATED APPLICATIONS

The present application is a continuation of U.S. patent application Ser. No. 16/105,299, filed Aug. 20, 2018, which is a divisional of U.S. patent application Ser. No. 15/640,781, filed Jul. 3, 2017, now U.S. Pat. No. 10,052,379, issued Aug. 21, 2018, which is a divisional of U.S. patent application Ser. No. 14/775,644, filed Sep. 11, 2015, now U.S. Pat. No. 9,694,069, issued Jul. 4, 2017, which is the U.S. national phase of International Application No. PCT/US2014/027585, filed Mar. 14, 2014, which designated the United States and which claims priority to provisional U.S. patent application No. 61/785,538, filed Mar. 14, 2013, and to provisional U.S. patent application No. 61/952,719, filed Mar. 13, 2014, each of which are hereby incorporated in their entireties.

FIELD OF THE INVENTION

The present invention relates to novel 6-acetylmorphine analogs useful for preparing conjugates comprising, inter alia, proteins, polypeptides, and labels; to conjugates comprising such 6-acetylmorphine analogs, and to methods for their synthesis and use.

BACKGROUND OF THE INVENTION

The following discussion of the background of the invention is merely provided to aid the reader in understanding the invention and is not admitted to describe or constitute prior art to the present invention.

6-Monoacetylmorphine (6-MAM, also known as 6-acetylmorphine or 6-AM) is one of three active metabolites of heroin (diacetylmorphine), the others being morphine and morphine-6-glucuronide. 6-AM is rapidly created from heroin in the body, and then is either metabolized into morphine or excreted in the urine. Since 6-AM is a unique metabolite to heroin, identification of 6-AM is considered to be definitive evidence of heroin use. This is significant because on a urine immunoassay drug screen, the test typically tests for morphine, which is a metabolite of a number of legal and illegal opiates/opioids such as codeine, morphine sulfate, and heroin. 6-AM remains in the urine for no more than 24 hours so a urine specimen must be collected soon after the last heroin use, but the presence of 6-AM guarantees that heroin was in fact used as recently as within the last day.

In developing a binding assay for 6-AM, the artisan must consider that samples may contain these metabolites of opiates/opioids. Thus, immunogenic and label conjugates should be designed to present 6-AM so as to provide an assay with minimal cross-reactivity to morphine, morphine-3-glucuronide, morphine-6-glucuronide and other opioids. Analogs for use in preparing such conjugates should also be designed to provide convenient attachment to various proteins, polypeptides, and labels under mild conditions.

BRIEF SUMMARY OF THE INVENTION

It is an object of the invention to provide novel 6-AM analogs, and methods for their synthesis and use. Such analogs are preferably designed to provide a reactive thiol (—SH) group, providing a linkage chemistry for convenient coupling to a suitable group on a target protein, polypeptide, or label.

For purposes of the following discussion, the following depicts the position numbering used in the art for morphine:

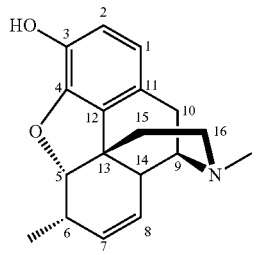

Thus, 6-AM has the following structure:

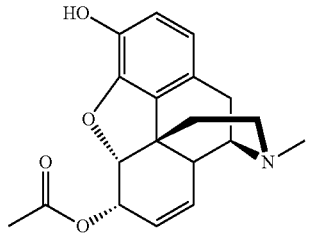

In a first aspect then, the invention relates to compounds (or salts thereof) having a general formula selected from (I), (II), (III), or (IV):

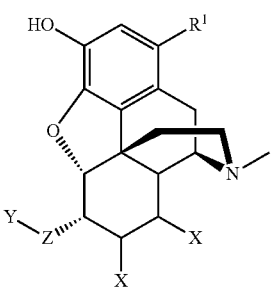

(I)

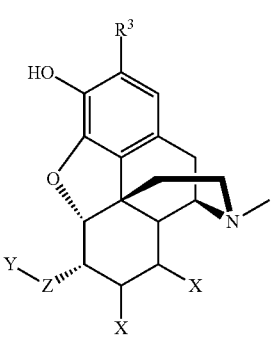

(II)

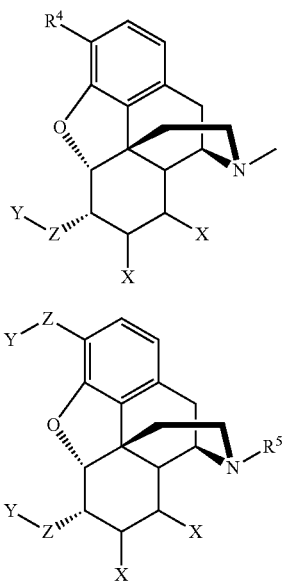

Most preferably —Z—Y is

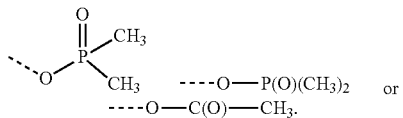

In certain embodiments, R1, R3, R4, or R5 is a linking group having the structure Q-J, where Q is a linker that is saturated or unsaturated, substituted or unsubstituted, aromatic or aliphatic, straight or branched chain of 0-10 carbon or heteroatoms (N, O, S), with an optional C(O), S(O) or $S(O_2)$; and J is a functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties.

In certain preferred embodiments, R1, R3, R4, or R5 is a linking group having the structure

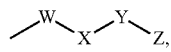

where

R1, R3, R4, or R5 is a linkage chemistry which provides a terminal functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties;

each Z is independently optionally substituted $C_{1-4}$ alkyl, $C_{1-4}$ alkoxy, N, O, S, and aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$, and where Z is preferably O, S, N, NH, $CH_3$, $CH_2$, CH, CHF or $CF_2$, and where Z is most preferably —C(O)—, —N(H)— or —O—;

each Y is independently selected from the group consisting of

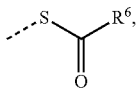

wherein each R2 is independently optionally substituted $C_{1-4}$ alkyl, $C_{1-4}$ alkoxy, OH, N, O, S, and aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$, and where each R2 is preferably $CH_3$, $CF_3$, $CHF_2$, $CH_2F$ or $NH_2$; and each X is H or together form a covalent bond.

where
W is $C_{0-4}$ unsubstituted alkyl;
X is an optionally present C(O);
Y is an optionally substituted $C_{0-4}$ alkyl or N(H)—$C_{0-6}$ alkyl, and is optionally present; and
Z is a functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties.

The choice of functional moiety may be varied by the artisan, depending on the desired length and composition for a crossbridge to a protein, polypeptide or label, and whether the functional moiety is in free or in protected form. In the latter case, a wide variety of protective groups for such functional moieties are known in the art. See, e.g., standard reference works such as Greene and Wuts, PROTECTIVE GROUPS IN ORGANIC SYNTHESIS, 3rd edition, John Wiley & Sons Inc., 1999, which is hereby incorporated by reference in its entirety. By way of example only, suitable thiol protective groups include thioesters, thioethers, unsymmetrical disulfides, and sulfenyls.

In preferred embodiments, the functional moiety is a 5- or 6-member cyclic thiolactone, an optionally substituted $C_{1-4}$ alkyl thiol, or an optionally substituted thioester having the structure where R6 is selected from the group consisting of optionally substituted $C_{1-4}$ alkyl, $C_{1-4}$ alkoxy, and aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$.

In a related aspect, the invention relates to compositions comprising one or more of the foregoing compounds (or their salts) covalently linked through the terminal functional moiety provided by R1 R3, or R4 to a protein, polypeptide, label, or other molecule, referred to herein as "6-AM analog conjugates."

In this aspect, the invention relates to compounds (or salts thereof) having a general formula selected from (V), (VI), (VII) or (VIII):

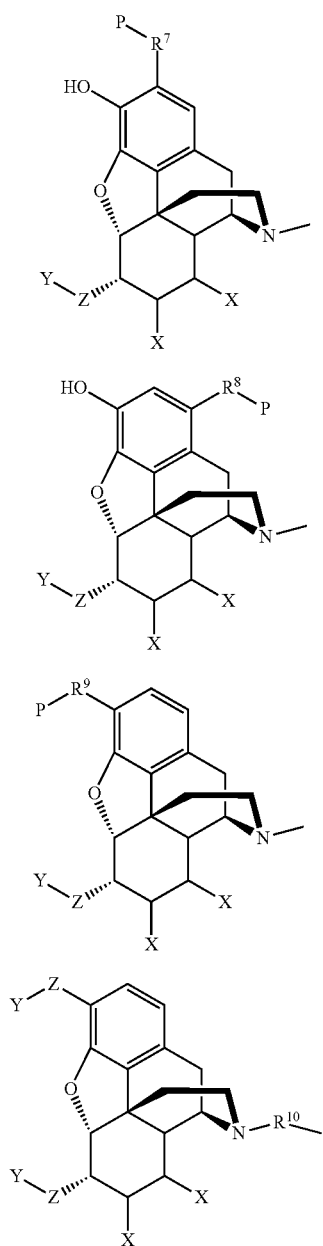

(V)

(VI)

(VII)

(VIII)

where
R7, R8, R9, or R10 is a linkage chemistry and P is a protein, polypeptide, label, or other molecule, wherein R7, R8, R9, or R10 and P are covalently linked;
each Z is independently optionally substituted $C_{1-4}$ alkyl, $C_{1-4}$ alkoxy, N, O, S, and aryl, wherein substitution(s), when present, may be independently selected from the group consisting of $C_{1-6}$ alkyl straight or branched chain, benzyl, halogen, trihalomethyl, $C_{1-6}$ alkoxy, —NO$_2$, —NH$_2$, —OH, =O, —COOR' where R' is H or lower alkyl, —CH$_2$OH, and —CONH$_2$, and where Z is preferably O, S, N, NH, CH$_3$, CH$_2$, CH, CHF or CF$_2$, and where Z is most preferably —C(O)—, —N(H)— or —O—.

each Y is independently selected from the group consisting of

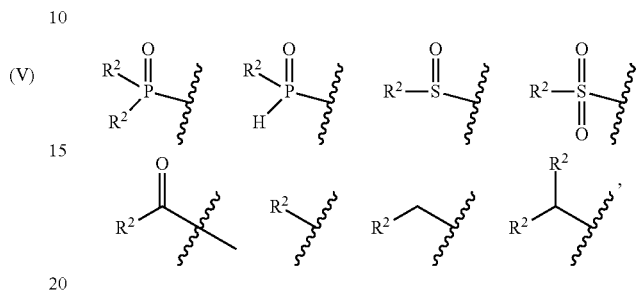

wherein each R2 is independently optionally substituted $C_{1-4}$ alkyl, $C_{1-4}$ alkoxy, OH, N, O, S, and aryl, wherein substitution(s), when present, may be independently selected from the group consisting of $C_{1-6}$ alkyl straight or branched chain, benzyl, halogen, trihalomethyl, $C_{1-6}$ alkoxy, —NO$_2$, —NH$_2$, —OH, =O, —COOR' where R' is H or lower alkyl, —CH$_2$OH, and —CONH$_2$, and where each R2 is preferably CH$_3$, CF$_3$, CHF$_2$, CH$_2$F or NH$_2$; and each X is H or together form a covalent bond.

Most preferably each R2 is methyl and Z is N(H), such that —Z—Y is.

In certain embodiments, R7, R8, R9, or R10 is a linking group having the structure Q-J, where Q is a linker that is saturated or unsaturated, substituted or unsubstituted, aromatic or aliphatic, straight or branched chain of 0-10 carbon or heteroatoms (N, O, S), with an optional C(O), S(O) or S(O$_2$); and J is a functional moiety conjugated to P via a linkage chemistry selected from the group consisting of sulfhydryl moieties, amine moieties carboxyl moieties, arginine moieties, and carbonyl moieties.

In certain preferred embodiments, R7, R8, R9, or R10 is a linking group having the structure

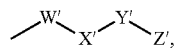

where
W' is $C_{0-4}$ unsubstituted alkyl;
X' is an optionally present C(O);
Y' is an optionally substituted $C_{0-4}$ alkyl or N(H)—$C_{0-6}$ alkyl, and is optionally present; and
Z' is a functional moiety selected from the group consisting of protected or unprotected sulfhydryl moieties, protected or unprotected amine moieties, primary amine-reactive moieties, sulfhydryl-reactive moieties, photoreactive moieties, carboxyl-reactive moieties, arginine-reactive moieties, and carbonyl-reactive moieties.

The compounds of the present invention may be directly linked to an appropriate target protein, polypeptide, label, or other molecule to form a conjugate via a coupling group naturally occurring in the target molecule, or by adding a coupling group to the target molecule. Exemplary coupling groups are described hereinafter, and methods for incorporating such coupling groups into target molecules for conjugation to the compounds described above are well known in the art. In the case of compounds of the invention comprising a protected functional moiety, removal of the protective group is performed by methods known in the art.

Preferred coupling groups on target molecules are maleimides, which are linked according to the following reaction scheme:

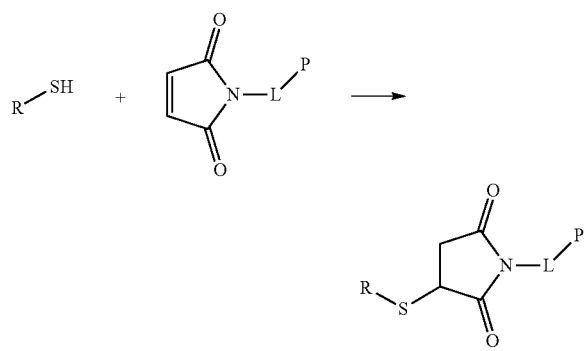

where R—SH is a compound of the invention comprising a free thiol (either as a free thiol or following deprotection of a protected thiol), L is a linkage chemistry, and P is a target protein, polypeptide, label, or other molecule. L is preferably $C_{1-10}$ alkylene straight or branched chain comprising from 0-4 backbone (i.e., non-substituent) heteroatoms, optionally substituted with from 1 to 4 substituents independently selected from the group consisting of $C_{1-6}$ alkyl straight or branched chain, —$NO_2$, —$NH_2$, =O, halogen, trihalomethyl, $C_{1-6}$ alkoxy, —OH, —$CH_2OH$, and —$C(O)NH_2$.

In certain embodiments, P is a protein, most preferably an antigenic protein which can be used to raise an immune response to an epitope on the compound of the invention using a so-called "hapten-carrier" immunogen. Common carrier proteins include bovine serum albumin, keyhole limpet hemocyanin, ovalbumin, etc. Protocols for conjugation of haptens to carrier proteins may be found in ANTIBODIES: A LABORATORY MANUAL, E. Harlow and D. Lane, eds., Cold Spring Harbor Laboratory (Cold Spring Harbor, N.Y., 1988) pp. 78-87, which is hereby incorporated by reference.

Alternatively, P may preferably be a detectable label. Preferred detectable labels may include molecules or larger structures that are themselves detectable (e.g., fluorescent moieties, electrochemical labels, metal chelates, latex particles, etc.), as well as molecules that may be indirectly detected by production of a detectable reaction product (e.g., enzymes such as horseradish peroxidase, alkaline phosphatase, etc.) or by a specific binding molecule which itself may be detectable (e.g., biotin, avidin, streptavidin, digoxigenin, maltose, oligohistidine, 2,4-dintrobenzene, phenylarsenate, ssDNA, dsDNA, etc.). Exemplary conjugation to such detectable labels is described hereinafter. Particularly preferred detectable labels are fluorescent latex particles.

The foregoing lists of suitable target molecules are not meant to be limiting. Further exemplary embodiments are described hereinafter. In addition, numerous other classes of suitable targets, including peptide hormones, therapeutic proteins, antibodies, antibody fragments, single-chain variable region fragments, small molecules, nucleic acids, oligosaccharides, polysaccharides, cyclic polypeptides, peptidomimetics, aptamers and solid phases are known in the art.

While a conjugation target may be conjugated 1:1 with a 6-AM analog of the invention, an individual target may also comprise more than 1 conjugation site, and hence more than 1 compound of the invention may be conjugated thereto. In preferred embodiments, a conjugation target (e.g., a protein, peptide, or label) comprises at least 10 6-AM analog moieties covalently bound thereto, more preferably at least 30, still more preferably at least 50, and most preferably at least 100.

In still other related aspects, the present invention relates to methods for the production and use of the 6-AM analogs of the present invention to form conjugates with a protein, polypeptide, label, or other molecule.

Such methods can comprise contacting one or more compounds of the invention comprising a reactive moiety (e.g., comprising a free thiol) with one or more target molecules comprising one or more corresponding coupling sites, under conditions where the reactive moiety(s) react with the coupling site(s) to form one or more conjugates. Conditions for such reactions are dependent upon the reactive moiety(s) selected, and are well known to the skilled artisan. Exemplary conditions are described hereinafter.

Such methods may further comprise the step of deprotecting a protected reactive moiety from one or more compounds of the invention prior to said contacting step, and/or attaching one or more coupling sites to a protein, polypeptide, label, or other molecule to form an appropriate conjugation target. In the latter case, this may comprise the use of bifunctional cross-linkers that provide an appropriate coupling sites at one site in the molecule, and a second coupling group for attachment to the protein, polypeptide, label, or other molecule of interest. Numerous bifunctional cross-linkers are well known to those of skill in the art.

Regarding the use of such 6-AM analog conjugates, the present invention relates to methods for preparing an antibody. These methods comprise using one or more conjugates as an immunogen to stimulate an immune response.

In certain embodiments, methods may comprise administering one or more conjugates of the invention in a suitable immunization protocol, and separating an appropriate antibody from a body fluid of the animal. Exemplary protocols for preparing immunogens, immunization of animals, and collection of antiserum may be found in ANTIBODIES: A LABORATORY MANUAL, E. Harlow and D. Lane, eds., Cold Spring Harbor Laboratory (Cold Spring Harbor, N.Y., 1988) pp. 55-120, which is hereby incorporated by reference. Alternatively, the 6-acetylmorphine analog conjugates of the present invention may be used in phage display methods to select phage displaying on their surface an appropriate antibody, followed by separation of nucleic acid sequences encoding at least a variable domain region of an appropriate antibody. Phage display methods are well known to those of skill in the art. Such methods may use immunized or unimmunized animals as a source of nucleic acids to form the phage display library. Antibodies prepared in this manner may preferably find use as therapeutic molecules and/or as receptors in receptor binding assays.

Preferably, such antibodies bind 6-AM with an affinity that is at least a factor of 5, more preferably at least a factor of 10, still more preferably at least a factor of 30, and most preferably at least a factor of 50 or more, than an affinity for morphine, morphine-3-glucuronide, and/or morphine-6-glucuronide.

Antibodies prepared in this manner may be used as specific binding reagents in immuoassays for determining 6-AM concentrations in samples. By way of example, a method can comprise performing a competitive immunoassay in using a conjugate having a general formula selected from (IV), (V), or (VI) in which P is a detectable label, the method comprising determining the concentration of 6-AM in the sample from the assay signal. Preferably, immunoassays provide a signal that is at least a factor of 5, more preferably at least a factor of 10, still more preferably at least a factor of 30, and most preferably at least a factor of 50 or more for 10 µg/mL 6-AM, compared to the signal obtained from 10 µg/mL, and more preferably 1000 µg/mL, morphine, morphine-3-glucuronide, and/or morphine-6-glucuronide.

Other embodiments of the invention will be apparent from the following detailed description, exemplary embodiments, and claims.

DETAILED DESCRIPTION OF THE INVENTION

Figure 1A:
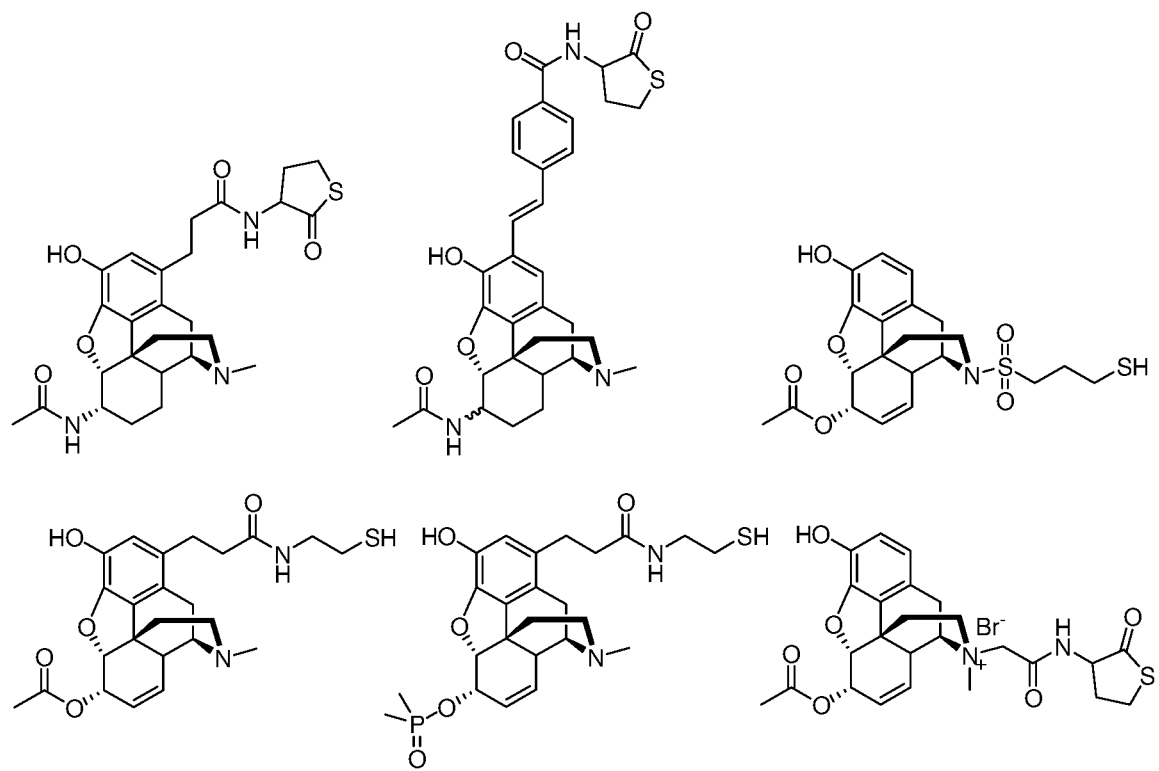
FIGS. 1A through 1E depict exemplary 6-AM analogs of the present invention.
Figure 1B:
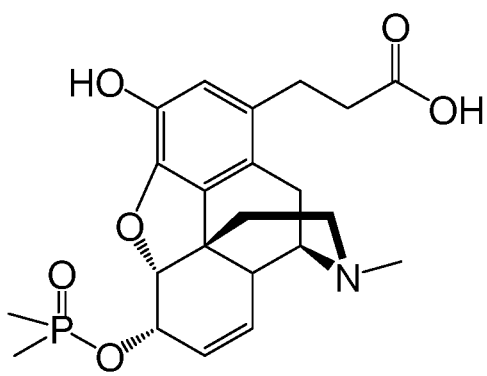
Figure 1B:
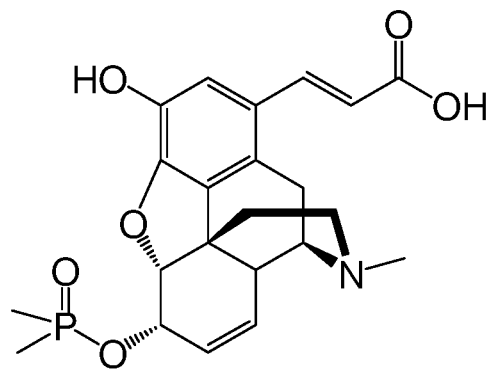
Figure 1B:
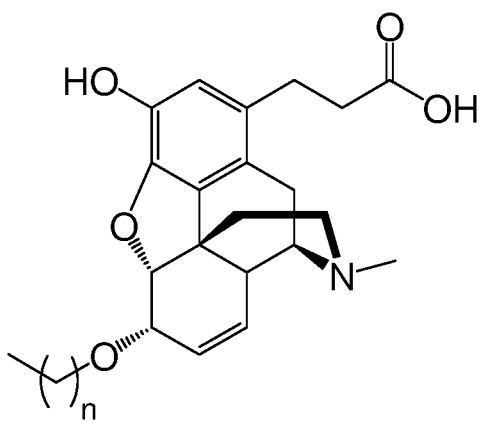
Figure 1B:
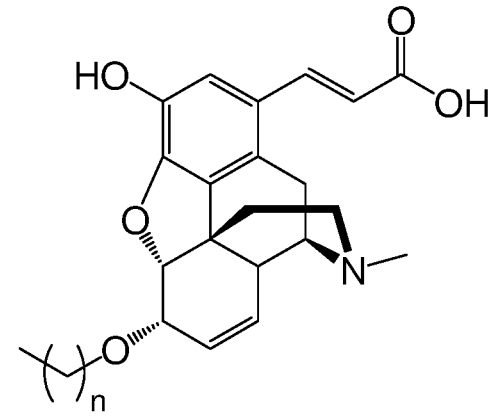
Figure 1C:
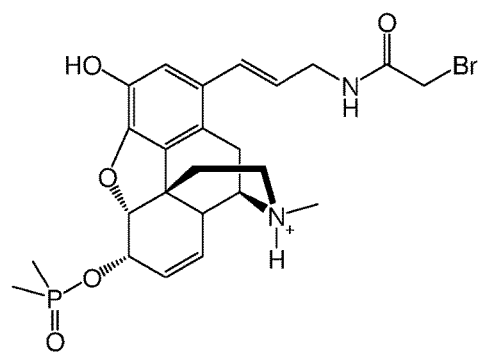
Figure 1C:
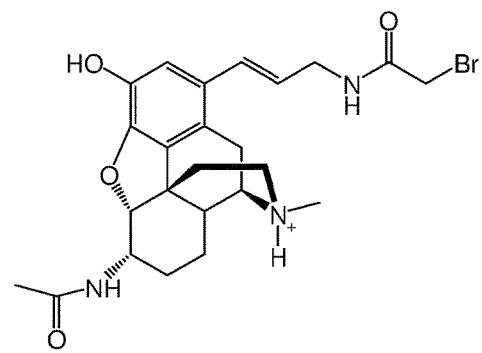
Figure 1C:
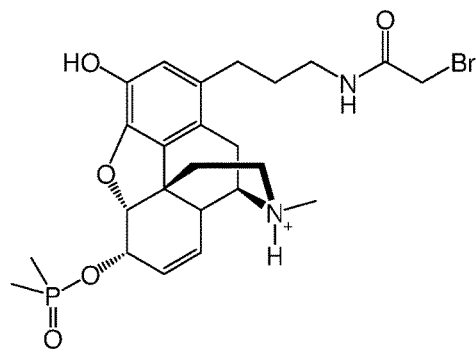
Figure 1C:
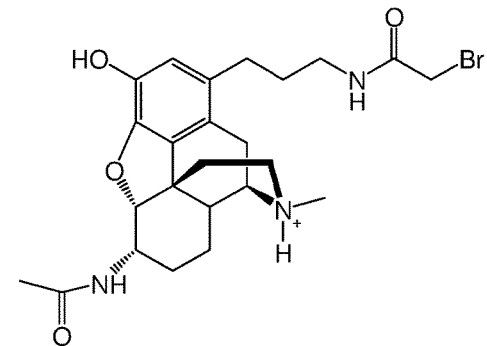
Figure 1D:
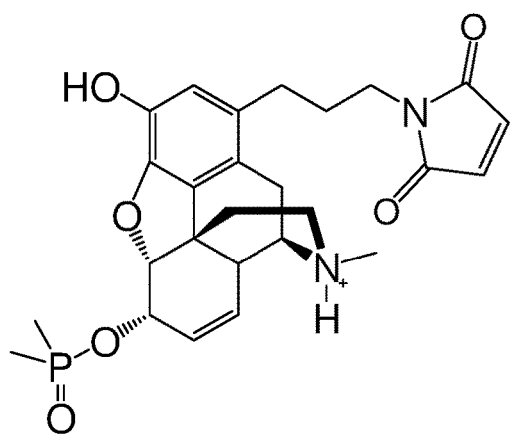
Figure 1D:
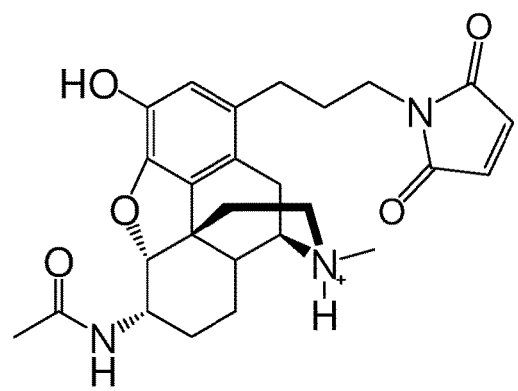
Figure 1D:
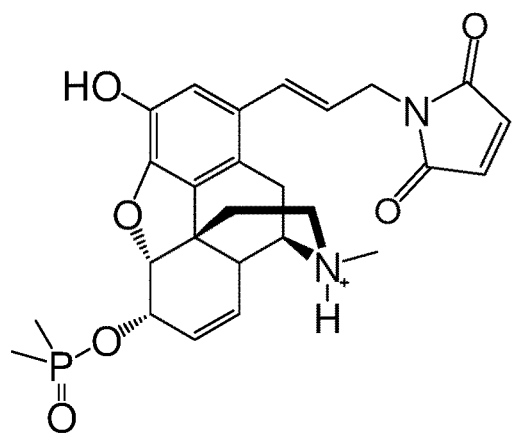
Figure 1D:
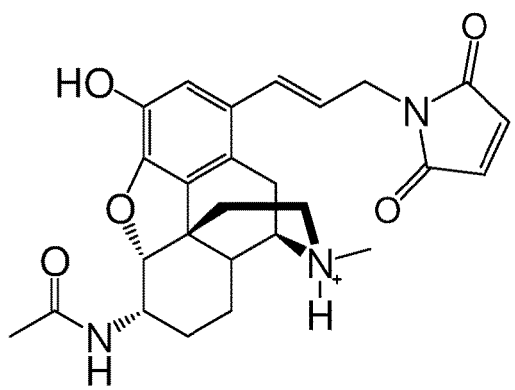
Figure 1E:
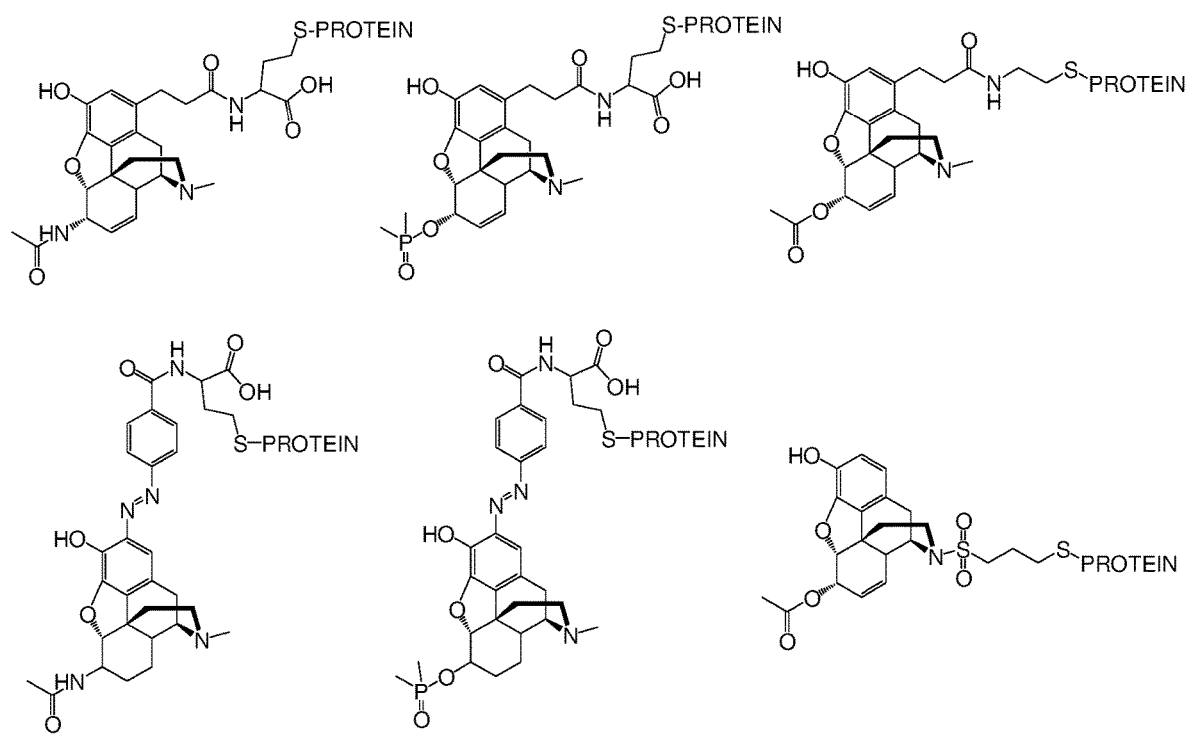

The present invention relates in part to 6-AM analogs and methods for their production and use, particularly for preparing cross-linkable thiol-containing 6-AM analogs for conjugation to another molecule, and for use of such conjugates for preparing reagents for immunoassays that detect 6-AM. The analogs of the present invention are particularly well suited for producing antibodies and labels for use in receptor binding assays for 6AM that can distinguish 6-AM from morphine, morphine-3-glucuronide, morphine-6-glucuronide and other opioids.

For the sake of clarity, definitions for the following terms regarding the compounds of the present invention are provided.

As used herein, the term "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. Preferably, the aryl is either optionally substituted phenyl, optionally substituted pyridyl, optionally substituted benzothiopyranyl, optionally substituted carbazole, optionally substituted naphthyl, optionally substituted tetrahydronaphthyl. While "aryl" is most preferably a monocyclic carbocyclic aromatic ring having 5 or 6 ring atoms (and is most preferably phenyl), the aryl or heteroaryl Ar group (formed into an arylene or heteroarylene in the crosslinkers described herein by elaboration from a ring atom) generally may contain up to ten ring atoms, although the skilled artisan will recognize that aryl groups with more than ten ring atoms are within the scope of the invention. The ring systems encompassed by Ar can contain up to four heteroatoms, independently selected from the group consisting of N, S, and O.

Monocyclic aryl groups include, but are not limited to: phenyl, thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Fused bicyclic Ar groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties.

As used herein, the term "heteroatom" refers to non-carbon, non-hydrogen atoms such as N, O, and S.

The aryl group may also be optionally substituted by replacement of one or more hydrogen atoms by another chemical moiety. Preferred substituents include $C_{1-6}$ alkyl straight or branched (e.g. isopropyl) chain, halogen, trihalomethyl, alkoxy, $NO_2$, $NH_2$, OH, —COOR', where R' is H or lower alkyl, $CH_2OH$, and $CONH_2$.

As used herein, the term "alkyl" refers to a saturated aliphatic hydrocarbon including straight chain and branched chain groups. Preferably, the alkyl group has 1 to 20 carbon atoms. More preferably, it is a medium alkyl (having 1 to 10 carbon atoms). Most preferably, it is a lower alkyl (having 1 to 4 carbon atoms). The alkyl group may be substituted or unsubstituted.

As used herein, the term "alkoxy" group refers to both an —O-alkyl and an —O-cycloalkyl group; preferably an alkoxy group refers to a lower alkoxy, and most preferably methoxy or ethoxy.

As used herein, the term "thiolactone" refers to a cyclic hydrocarbon having 5 or 6 ring atoms, one of which is an S heteroatom, and where the heteroatom is adjacent to a carbon substituted with a =O.

As used herein, the term "thioester" refers to an organic compound having the structure R—S—C(O)—R'.

As used herein, the term "alkyl thiol" refers to an alkyl group containing an —SH group. Thiols are also referred to as "thio alcohols" and "sulfhydryls."

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3rd Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and $CH_1$ domains; (ii) a F(ab')2 fragment, a bivalent fragment comprising two Fab fragments linked by a disulfide bridge at the hinge region; (iii) a Fd fragment consisting of the VH and $CH_1$ domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

The term "polypeptide" as used herein refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and derivatives. The term protein refers to a polypeptide that is isolated from a natural source, or produced from an isolated cDNA using recombinant DNA technology, and that has a sequence of amino acids having a length of at least about 200 amino acids.

The term "nucleic acids" as used herein shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of purine or pyrimidine bases, or modified purine or pyrimidine bases.

The term "aptamer" as used herein is a single-stranded or double-stranded oligodeoxyribonucleotide, oligoribonucleotide or modified derivatives that specifically bind and alter the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The term "polysaccharide" as used herein refers to a molecule comprising more than 10 glycosidically linked monosaccharide residues, while the term "oligosaccharide" refers to a molecule comprising from 2-10 glycosidically linked monosaccharide residues.

The term "small molecule" includes any molecule having a molecular weight less than about 5,000 daltons (Da), preferably less than about 2,500 Da, more preferably less than 1,000 Da, most preferably less than about 500 Da.

Functional Moieties

Chemical cross-linkers are valuable tools for preparing antibody-detectable label conjugates, immunotoxins and other labeled protein and nucleic acid reagents. These reagents may be classified on the basis of the following:

1. Functional groups and chemical specificity;
2. length and composition of the cross-bridge;
3. whether the cross-linking groups are similar (homobifunctional) or different (heterobifunctional);
4. whether the groups react chemically or photochemically;
5. whether the reagent is cleavable; and
6. whether the reagent can be radiolabeled or tagged with another label.

As the compounds of the present invention provide an available thiol to act as an attachment point, targets may be prepared to provide an appropriate thiol-reactive site. Cross-linking reagents that couple through sulfhydryls (thiols) are available from many commercial sources. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Such reagents may be bifunctional, in that a second site on the reagent is available for use in modifying a conjugation target to incorporate the thiol-reactive site. In addition to thiols, reactive groups that can be targeted using a cross-linker include primary amines, carbonyls, carbohydrates and carboxylic acids. In addition, many reactive groups can be coupled nonselectively using a cross-linker such as photoreactive phenyl azides. Thus, a two-step strategy allows for the coupling of a protein that can tolerate the modification of its amines to a 6-acetylmorphine analog of the invention. For suitable reagents, see Pierce 2003-2004 Applications Handbook and Catalog #1600926, which is hereby incorporated by reference. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

Many factors must be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length cross-linkers and analyzing the success of conjugation. The use of cross-linkers with different reactive groups and/or spacer arms may be desirable when the conformation of the protein changes such that hindered amino acids become available for cross-linking.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, while intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380-8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety may be made empirically in order to best preserve a biological property of interest (e.g., binding affinity of an antibody, catalytic activity of an enzyme, etc.)

1. Coupling Through Amine Groups

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.

2. Coupling Through Sulfhydryl Groups

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

3. Coupling Through Carboxyl Groups

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

4. Nonselective Labeling

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

5. Carbonyl Specific Cross-Linkers

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

Exemplary Applications for Use of Cross-Linkable 6-Acetylmorphine Analogs

1. Carrier Protein-Hapten/Peptide/Polypeptide Conjugates for Use as Immunogens

Numerous companies offer commercially available products in this area of immunological research. There are many cross-linkers used for the production of these conjugates, and the best choice is dependent on the reactive groups present on the hapten and the ability of the hapten-carrier conjugate to function successfully as an immunogen after its injection. Carbodiimides are good choices for producing peptide carrier conjugates because both proteins and peptides usually contain several carboxyls and primary amines. Other cross-linkers can also be used to make immunogen conjugates.

Adjuvants are mixtures of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Adjuvants have four main modes of action: enhanced antigen uptake and localization, extended antigen release, macrophage activation, and T and B cell stimulation. The most commonly used adjuvants fall into six categories: mineral salts, oil emulsions, microbacterial products, saponins, synthetic products and cytokines. A more extensive discussion of adjuvants and their use in immunization protocols is given in IMMUNOLOGY METHODS MANUAL, vol. 2, I. Lefkovits, ed., Academic Press, San Diego, Calif., 1997, ch. 13, which is hereby incorporated in its entirety Small molecules such as 6-acetylmorphine are not usually immunogenic, even when administered in the presence of adjuvant. In order to generate an immune response to these compounds, it is often necessary to attach them to a protein or other compound, termed a carrier, that is immunogenic. When attached to a carrier protein the small molecule immunogen is called a hapten. Haptens are also conjugated to carrier proteins for use in immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore important to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Keyhole limpet hemocyanin (KLH) is a respiratory protein found in mollusks. Its large size makes it very immunogenic, and the large number of lysine residues available for conjugation make it very useful as a carrier for haptens such as 6-acetylmorphine. The phylogenic separation between mammals and mollusks increases the immunogenicity and reduces the risk of cross-reactivity between antibodies against the KLH carrier and naturally occurring proteins in mammalian samples.

2. Solid-Phase Immobilization

The analogs and/or conjugates of the present invention can be immobilized on solid-phase matrices for use as affinity supports or for sample analysis. Similarly, antibodies or their binding fragments made or selected using the 6-acetylmorphine analogs and/or conjugates of the present invention can also be immobilized on solid-phase matrices. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of Immunoassay, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001.

Surfaces such as those described above may be modified to provide linkage sites, for example by bromoacetylation, silation, addition of amino groups using nitric acid, and attachment of intermediary proteins, dendrimers and/or star polymers. This list is not meant to be limiting, and any method known to those of skill in the art may be employed.

3. Detectable Label Conjugates

Biological assays require methods for detection, and one of the most common methods for quantitation of results is to conjugate an enzyme, fluorophore or other detectable label to the molecule under study (e.g., using one or more analogs of the invention), which may be immobilized for detection by a receptor molecule that has affinity for the molecule. Alternatively, the receptor to the molecule under study (e.g., an antibody or binding fragment thereof made or selected using the analogs or conjugates of the invention) may be conjugated to an enzyme, fluorophore or other detectable label. Enzyme conjugates are among the most common conjugates used. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g, biotin, digoxigenin, maltose, oligohistidine, 2,4-dintrobenzene, phenylarsenate, ssDNA, dsDNA, etc.).

Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter.

Use of 6-AM Analogs in Receptor Binding Assays

6-AM analogs and conjugates of the present invention may be advantageously used in receptor binding assays. Receptor binding assays include any assay in which a signal is dependent upon specific binding of an analyte to a cognate receptor, and include immunoassays, ligand-receptor assays, and nucleic acid hybridization assays.

The presence or amount of an analyte is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Numerous methods and devices are well known to the skilled artisan for the practice of receptor binding assays. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize detectably labeled molecules and antibody solid phases in various sandwich, competitive, or non-competitive assay formats, to generate a signal that is related to the presence or amount of an analyte of interest. One skilled in the art also recognizes that robotic instrumentation including but not limited to Beckman Access, Abbott AxSym, Roche ElecSys, Dade Behring Stratus systems are among the immunoassay analyzers that are capable of performing such immunoassays. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. As described herein, preferred assays utilize an antibody raised against an analog conjugate (wherein the antibody is coupled to a solid phase or a detectable label), and/or a 6-acetylmorphine analog conjugated to a detectable label, and/or a 6-acetylmorphine analog conjugated to a solid phase.

In its simplest form, an assay device according to the invention may comprise a solid surface comprising receptor(s) that specifically bind one or more analytes of interest (e.g., 6-AM). For example, antibodies may be immobilized onto a variety of solid supports, such as magnetic or chromatographic matrix particles, the surface of an assay plate (such as microtiter wells), pieces of a solid substrate material or membrane (such as plastic, nylon, paper), and the like using the cross-linkers of the present invention. In similar fashion, an assay device may comprise a solid surface comprising one or more of the 6-AM analogs described herein immobilized thereon.

The analysis of a plurality of analytes may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of analytes on a single surface. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

Figure 2:
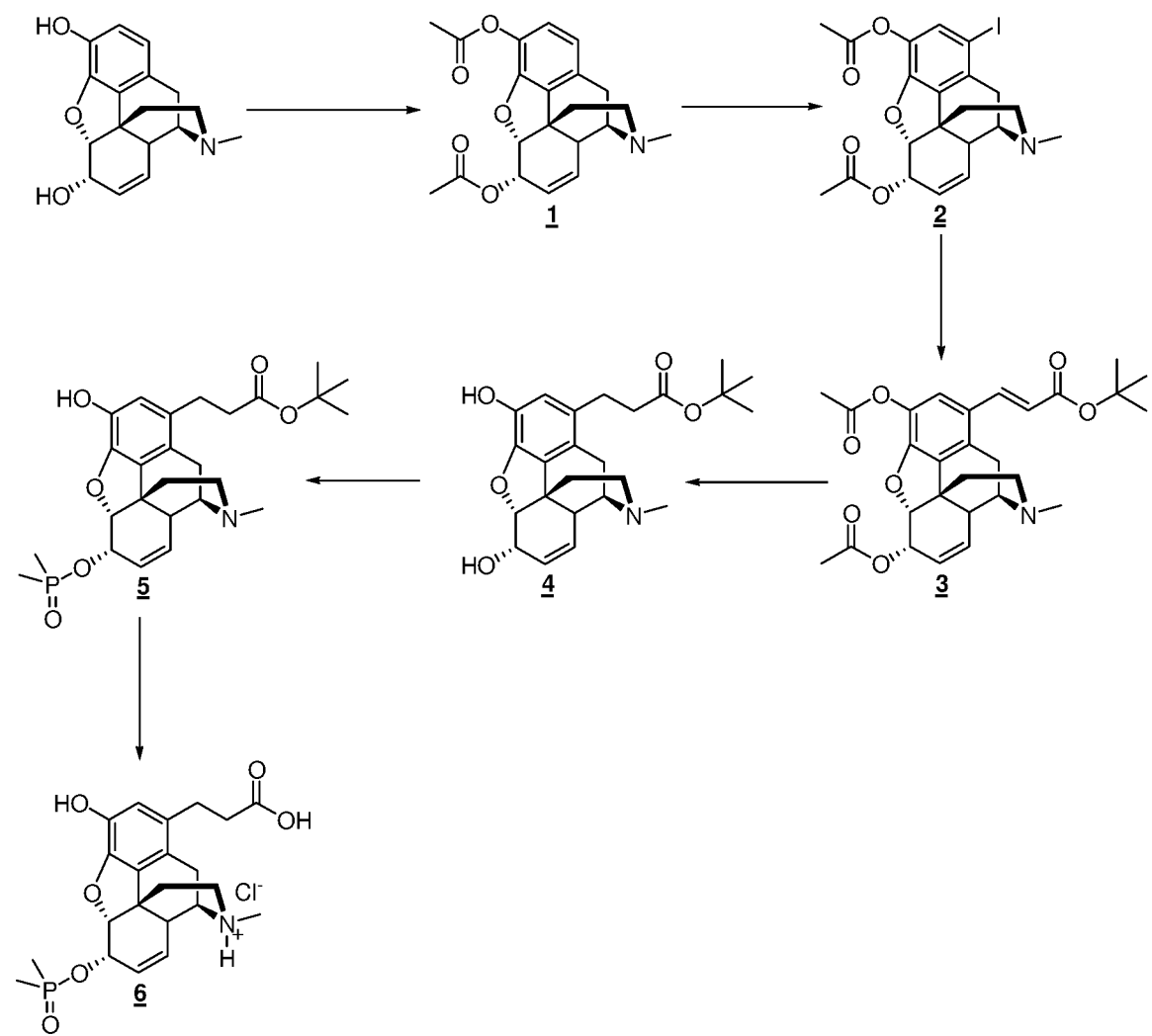
FIG. 2 depicts reaction schemes to prepare exemplary 6-AM analogs of the present invention.
Figure 3:
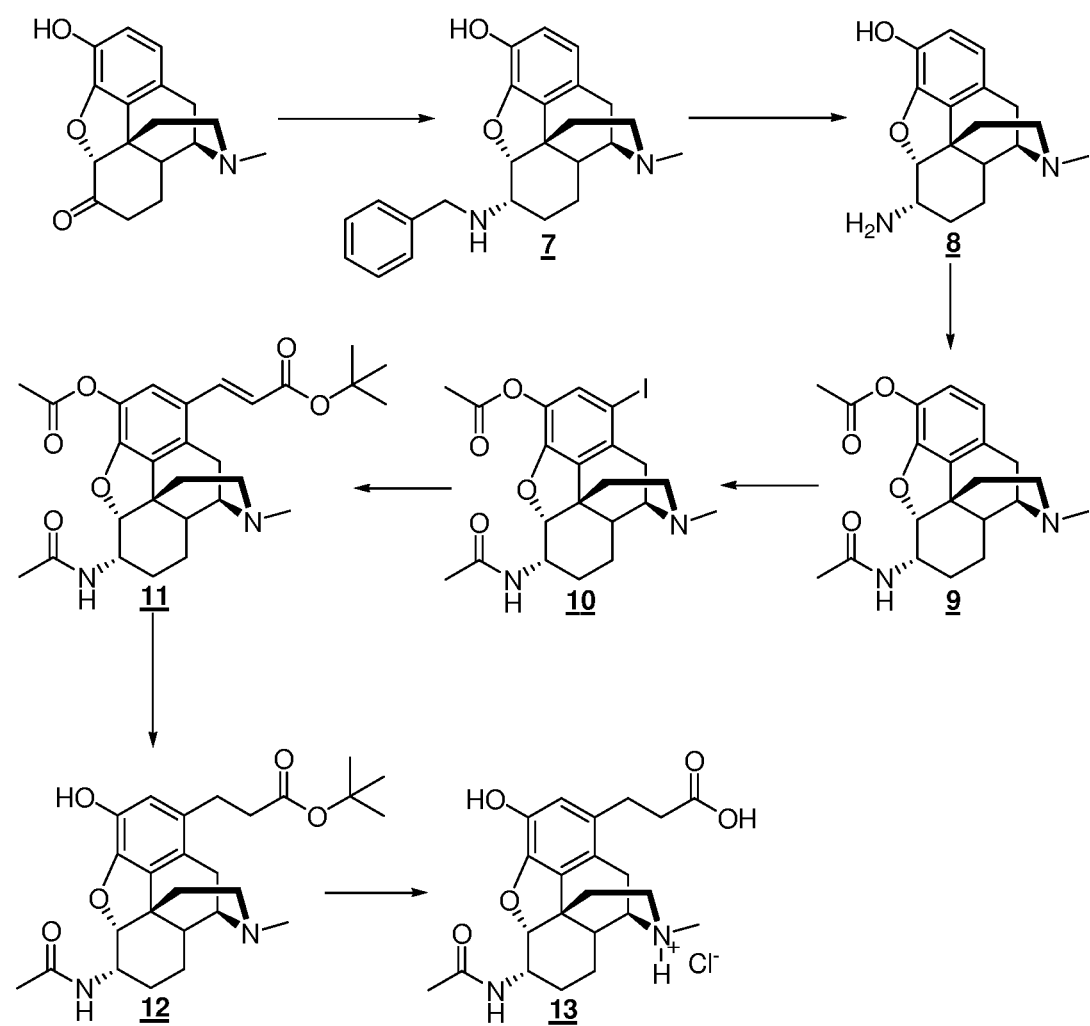
FIG. 3 depicts depict reaction schemes to prepare exemplary 6-AM analogs of the present invention.
Figure 4:
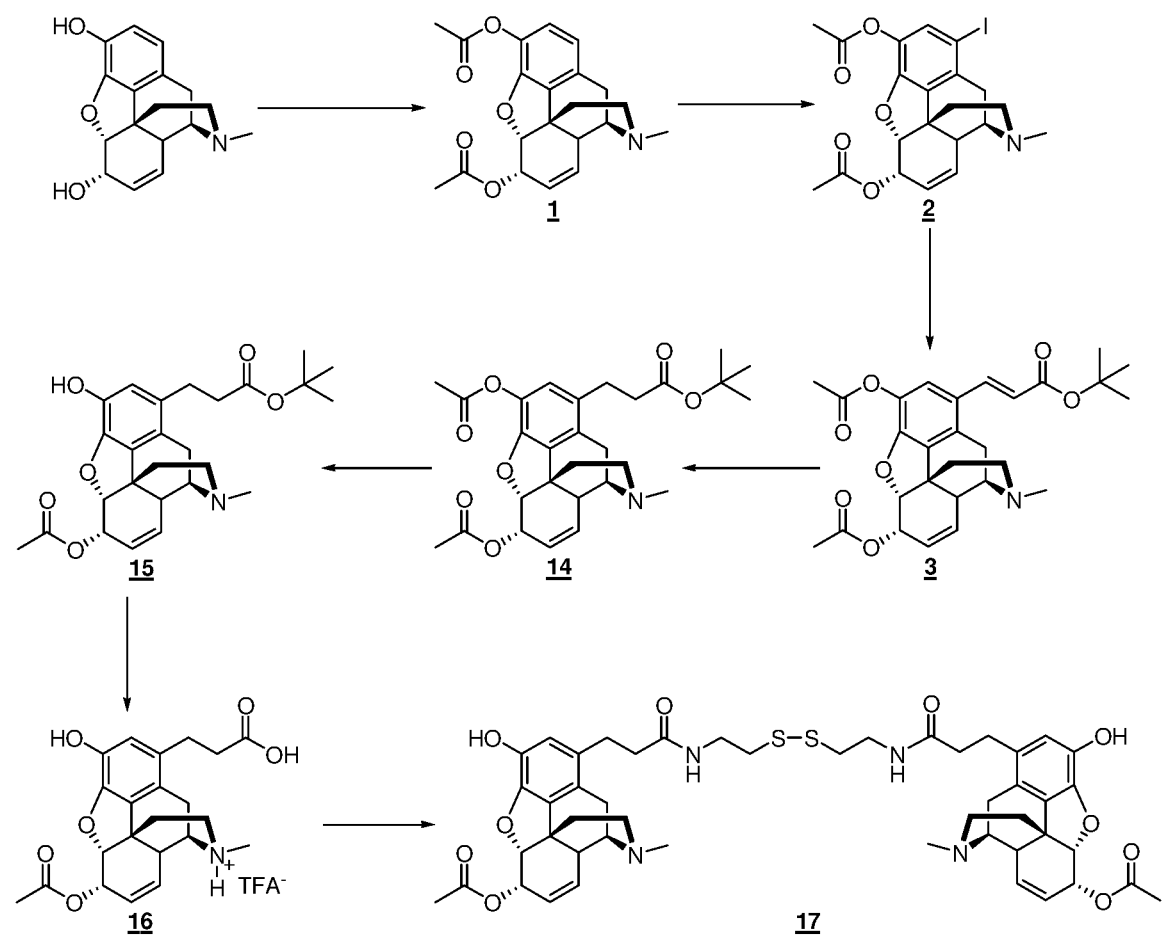
FIG. 4 depicts a reaction scheme to prepare exemplary 6-AM analogs of the present invention.
Figure 5:
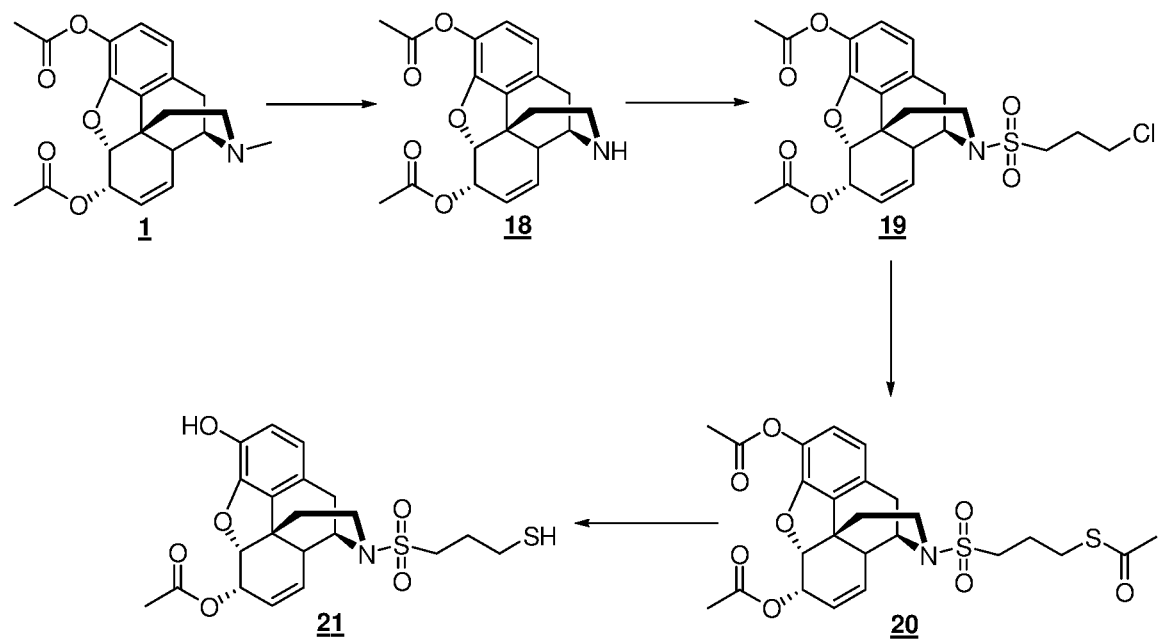
FIG. 5 depicts a reaction scheme to prepare exemplary 6-AM analogs of the present invention.
Figure 6:
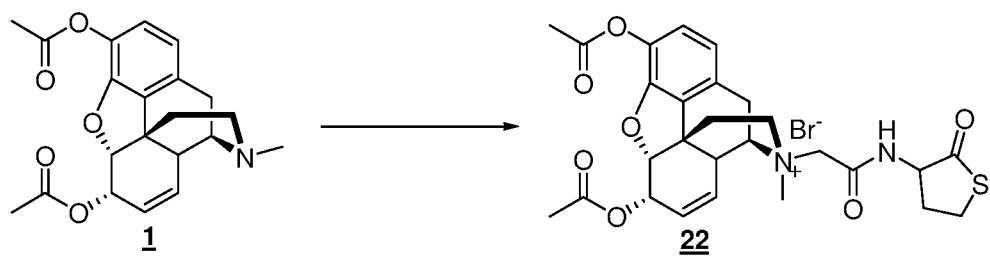
FIG. 6 depicts a reaction scheme to prepare exemplary 6-AM analogs of the present invention.

Preparation of 6-Acetyl Morphine (6AM) Derivatives at the 1-Position of the A Ring in the Morphine Scaffold The synthetic schemes are shown below and depicted in FIGS. 2-6. For the synthesis of 6-phosphinyl derivative 6, morphine sulfate may be acetylated to make diacetylmorphine, followed by iodination to yield 1-Iodo-diacetylmorphine derivative 2. Heck coupling of 2 with tert-butyl acrylate yields enoate 3, which may be selectively reduced using $Mg^0$/MeOH to give saturated diol 4. Phosphinylation of 4, followed by removal of the aryl Phosphinyl yielded 5, may be subsequently deprotected using acidic conditions to yield the 6-phosphinyl derivative 6 (FIG. 2). For the synthesis of 6-acetamide derivative 13, hydromorphine hydrochloride may be exposed to reductive amination with benzylamine, followed by reduction to yield 6-aminohydromorphine derivative 8. The 6-amino compound is acetylated, followed by iodination to yield 1-iodo-6-acetamide 10. Heck coupling of 10 with tert-butyl acrylate yields enoate 11, which may be reduced using $Mg^0$/MeOH to give saturated 6-acetamide 12. Acidic deprotection of 12 gives 6-acetamide derivative 13 (FIG. 3). For the synthesis of 6-acetyl disulfide 17, saturated diol 4 may be acetylated to give 14, followed by removal of the phenolic acetate with hydroxylamine to yield 15, and deprotection of the tert-butyl ester using acidic conditions to give carboxylic acid 16. Carboxylic acid 16 may then be coupled with cystamine to give 6-acetyl disulfide 17 (FIG. 4). For the synthesis of sulfonamide 21, diacetylmorphine may be N-demethylated to nor-diacetylmorphine 18, followed by formation of chloride 19. The chloride can then be displaced to yield thioacetate 20, which is then deprotected to give sulfonamide 21 (FIG. 5). For the synthesis of quaternary salt 22, diacetylmorphine 1 may N-alkylated with 2-bromo-N-acetyl-HCTL (FIG. 6).

Morphine sulfate pentahydrate and Hydromorphone hydrochloride may be obtained from Spectrum Chemical Company. $^1$H NMR spectra are typically taken in DMSO $D_6$ (from ampoules) or $CDCl_3$ at 500 MHz by NuMega Laboratories. HPLC is typically conducted using an Agilent Model 1200 machine equipped with either a Waters X-bridge (C18, 3.5 μm, 3.0×50 μm) or Fisher Thermo Hypercarb (5.0 um, 4.6×100 mm) columns. For HPLC, solvent A (95% $H_2O$/5% $CH_3CN$/0.1% TFA) and solvent B (95% $CH_3CN$/5% $H_2O$/0.1% TFA) may be used as described herein. HPLC runs may be either 6 or 15 minutes long. For the 6 minute run: 0 minutes, 5% B, 0-5 minutes, gradient to 100% B, 5-6 minutes, gradient to 5% B; for the 15 minute run: 0 minutes 0% B, 0-12 minutes, gradient to 100% B, 12-14 minutes 100% B, 14-15 minutes, gradient to 0% B. LC/MS may be conducted using a Waters model e2795 series LC equipped with a model 2996 photodiode array detector, a series 3100 MS and a Waters X-Bridge-C18 column, 3.5 um, 2.1×50 mm. For LC/MS, solvent A (95% $H_2O$/5% $CH_3CN$/0.1% Formic Acid) and solvent B (95% $CH_3CN$/5% $H_2O$/0.1% Formic Acid) may be used as described herein. HPLC runs may be 5 minutes: 0 minutes 0% B, 0-3.5 minutes, gradient to 100% B, 3.5-4.8 minutes 100% B, 4.8 to 4.9 minutes gradient to 0% B, 5.0 minutes, 0% B.

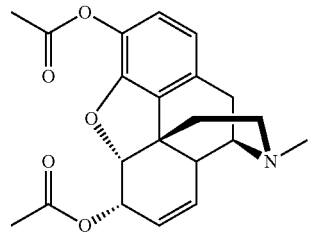

Diacetylmorphine (1): Morphine sulfate pentahydrate (1 g/1.32 mmol morphine sulfate pentahydrate/2.64 mmol morphine) is suspended in $CH_2Cl_2$ (10 mL) followed by the addition of $NEt_3$ (2.0 mL/14 mmol), pyridine (3 mL) and acetic anhydride (2.4 mL/25.4 mmol). The resulting suspension is stirred at room temperature for one hour, during which time all morphine sulfate went into solution. The solution is then stirred for 14 hours at room temperature. After this time period, additional acetic anhydride (200 μL/2.1 mmol) is added, and the solution is heated to 40° C. for 6 hours. The solution is then cooled to room temperature, MeOH (7 mL) is added, and the resulting solution stirred at room temperature for one hour before removal of the solvents under reduced pressure. The remaining residue is partitioned in a separatory funnel between EtOAc (90 mL) and saturated $NaHCO_3$ (45 mL), and the biphasic mixture shaken until a minimum amount of gas is discharged. The organic phase is washed with saturated $NaHCO_3$ (20 mL) and brine (20 mL) and dried with $MgSO_4$. The solvents are evaporated, and the resulting light brown residue placed under high vacuum overnight to afford diacetylmorphine (905 mg/70% yield). $^1$H NMR (500 MHz, DMSO $D_6$) δ 6.77 (d, J=8.5 Hz, 1H), 6.63 (d, J=8.0 Hz, 1H), 5.57 (m, 1H), 5.48 (m, 1H), 5.11 (m, 1H), 5.08 (m, 1H); LC/MS 370 (M+H$^+$).

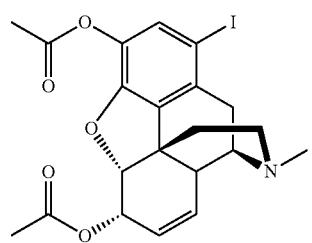

1-Iododiacetylmorphine (2): N-Iodosuccinimide (NIS) (427 mg/1.9 mmol) is added in one portion to a solution of 1 (460 mg/1.25 mmol) in 0.05 M $H_2SO_4$ (15 mL), and the resulting solution is stirred at room temperature for three hours before the addition of NIS (93 mg/0.4 mmol) in one portion. The reaction is then stirred at room temperature for three hours, after which time LC/MS indicated the reaction is complete. The reaction is then transferred to a separatory funnel containing 30 mL of EtOAc and the reaction vessel is washed well with EtOAc. Saturated NaHCO3 (20 mL) is then added and the separatory funnel is shaken. The layers are separated, and the aqueous layer is extracted with EtOAc (2×15 mL). The combined organics are washed with 2% sodium bisulfite (2×10 mL) and brine (1×10 ml), dried with $MgSO_4$, and the solvents removed under reduced pressure. The crude product is purified by ISCO (24 g column, 0-10% MeOH in $CH_2Cl_2$) to afford the pure product as a yellow solid (618 mg/94% yield). $^1$H NMR (500 MHz, DMSO D$_6$) δ 7.27 (s, 1H), 5.53 (app. q, 2H), 5.14 (m, 1H), 5.06 (d, J=6.5 Hz, 1H); LC/MS 496 (M+H$^+$).

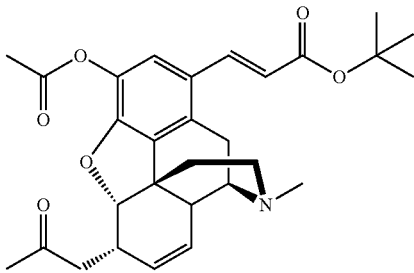

3

Anhydrous DMF (25 mL) is added to a vial containing 2 (1.19 g/2.4 mmol), and the solution is sparged with argon for 5 minutes, followed by the addition of bis(triphenylphosphine)palladium(II) dichloride (Pd(PPh$_3$)$_2$Cl$_2$) (0.17 g/0.24 mmol), tert-butyl acrylate (1.7 mL/11.7 mmol) and NEt$_3$ (1.3 mL/9.4 mmol). The resulting solution is heated to 90° C. for 6 hours, then cooled to room temperature. EtOAc (50 mL) is added, and the solution is transferred to a separatory funnel. The organic layer is washed with saturated aq NaHCO$_3$ (1×15 mL), and the aqueous layer is back extracted with EtOAc (2×15 mL). The combined organics are washed with brine (1×15 mL), dried with MgSO$_4$ and the solvent removed under reduced pressure. The crude product is purified by ISCO (24 g column, 0-10% MeOH in CH$_2$Cl$_2$) to afford enoate 3 as a yellow solid (795 mg/67% yield). $^1$H NMR (500 MHz, DMSO D$_6$) δ 7.62 (d, J=16 Hz, 1H), 7.35 (s, 1H), 6.27 (d, J=16 Hz, 1H), 5.52 (app. q, 2H), 5.14 (m, 1H), 5.10 (d, J=7 Hz, 1H), 1.47 (s, 9H); LC/MS 496 (M+H$^+$).

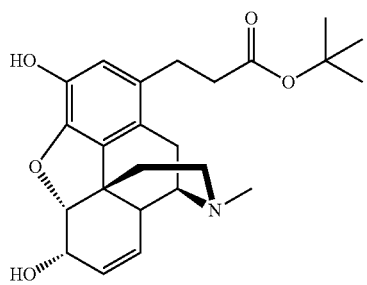

4

Enoate 3 (828 mg/1.67 mmol) is dissolved in MeOH (12 mL, Sigma-Aldrich, anhydrous), followed by the addition of magnesium turnings (280 mg/11.5 mmol) and the resulting solution is stirred at room temperature for 2 hours, after which time all Mg had dissolved. Additional Mg turnings are added (50 mg/2.1 mmol), and the reaction is stirred for 2 hours. The solvent is then removed under reduced pressure to yield a dark brown solid, which is dissolved in 10 mL of CHCl$_3$ (bath sonication is necessary to dissolve), and the solution is transferred to a 500 mL separatory funnel. The reaction vial is washed with CHCl$_3$ (3×10 mL), and 20 mL of CHCl$_3$ is added to the separatory funnel, followed by the addition of 15 mL of brine. Upon the addition of brine, an emulsion is formed. An additional 30 mL of CHCl$_3$ is added to the funnel, and the suspension is separated by draining the organic phase into a 1 L Erlenmeyer flask. The remaining aqueous layer is extracted with CHCl$_3$ (6×35 mL), and the combined organic phases are dried overnight by stirring with 37 g of sodium sulfate. After overnight stirring, the organic phase is cloudy. The solution is filtered over celite. The celite is washed with CHCl$_3$ (3×40 mL), and the solvents are evaporated to obtain 4 as an amorphous solid (230 mg/33% yield) that is used without further purification in the next step. LC/MS 414 (M+H$^+$).

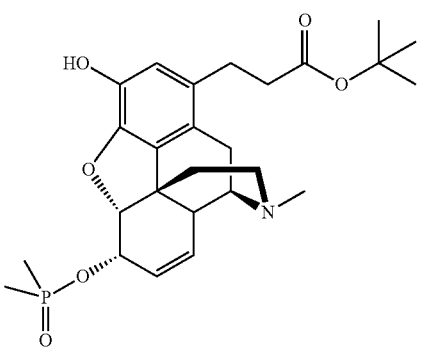

5

Dimethylphosphinyl chloride is added in one portion to an oven dried 250 mL round bottom flask, followed by the addition of pyridine (anhydrous, 5 mL), and the resulting solution is cooled to 0° C. in an ice bath for 30 minutes before the addition of tetrazole (16 mL of a 3% by mass solution in CH$_3$CN) in one portion. The resulting solution is stirred at 0° C. for 10 minutes before the addition of a solution of diol (crude Mg reduction material 4 was) in pyridine (anhydrous, 5 mL) at the same temperature. The solution is stirred at 0° C. for 10 minutes, followed by removal of the ice bath and allowed to warm to room temperature for two hours. After this time period, LC MS indicated the reaction is complete, only the mass of the diphosphinyl product is observed. Pyridine solvent is then removed under reduced pressure (residual pyridine is present). After removal of most of the pyridine, 30 mL of saturated NaHCO$_3$ is added, followed by 15 mL of MeOH. The resulting solution is stirred at room temperature for 48 hours. The solution is transferred to a 250 mL separatory funnel, and the reaction flask is washed with CH$_2$Cl$_2$ (2×15 mL). 20 mL of CH$_2$Cl$_2$ is added to the separatory funnel, followed by 10 mL of brine. The funnel is gently shaken, and the organic layer is separated. The aqueous layer is extracted with CH$_2$Cl$_2$ (3×20 mL), the combined organic layers are dried with MgSO$_4$ and the solvents are removed under reduced pressure, The product is purified by ISCO using a 24 g silica column (100% CH$_2$Cl$_2$ to 80% CH$_2$Cl$_2$:20% CH$_2$Cl$_2$:MeOH:concentrated NH$_4$OH (8:2:0.001) to afford 5 (176 mg/65% from crude 4). $^1$H NMR (500 MHz, DMSO D$_6$) δ 8.81 (s, 1H), 6.32 (s, 1H), 5.55 (d, J=10 Hz, 1H), 5.38 (d, J=10 Hz, 1H), 4.83 (m, 1H), 4.77 (d, J=5 Hz, 1H), 1.55-1.44 (dd, J=15, 40 Hz, 6H), 1.37 (s, 9H); LC/MS 491 (M+H$^+$).

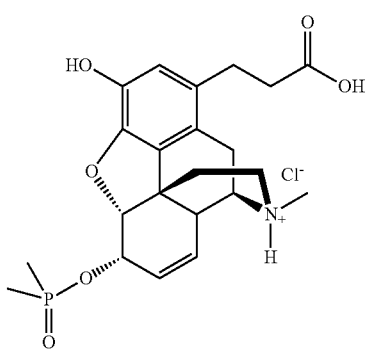

6

Tert-butyl ester 5 (171 mg/0.35 mmol) is dissolved in CH$_2$Cl$_2$ (3 mL) followed by the addition of TFA:CH$_2$Cl$_2$ (3 mL:1 mL). The resulting solution is stirred at room temperature for 2 hours, followed by removal of the solvents are removed under reduced pressure. The residue is then placed under high vacuum for 2 hours. After high vacuum, 1.5 mL of CH$_2$Cl$_2$ is added, followed by the addition of HCl in ether (450 uL). The solvents are evaporated, and the resulting solid is evaporated with CH$_2$Cl$_2$ (1×3 mL) and CH$_3$CN (2×3 mL), then placed under high vacuum overnight to give 6 as an off-white solid (159 mg/99% yield). $^1$H NMR (500 MHz, DMSO D$_6$) δ 9.10 (s, 1H), 6.44 (s, 1H), 5.69 (d, J=10 Hz, 1H), 5.42 (d, J=10 Hz, 1H), 4.95 (d, J=10 Hz, 1H), 4.86 (m, 1H), 1.57-1.46 (dd, J=15, 40 Hz, 6H); $^{31}$P NMR (125 MHz, CD$_3$OD) δ 60.47; LC/MS 434 (M+H$^+$ of free base).

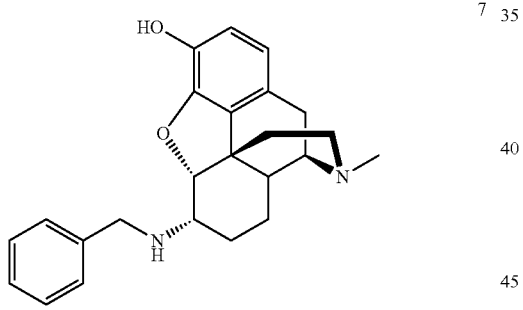

7

To an oven dried flask equipped with a magnetic stir bar is added hydromorphone HCl (469 mg/1.5 mmol) followed by suspending in 1,2-dichloroethane (anhydrous, 12 mL). To the resulting suspension is added benzylamine (192 μL/1.8 mmol) and sodium triacetoxyborohydride (592 mg/2.8 mmol). The resulting suspension is stirred overnight under argon at room temperature. The suspension is then transferred to a separatory funnel, and the reaction vial is washed with CH$_2$Cl$_2$ (3×10 mL). Saturated NaHCO$_3$ (10 mL) is added to the separatory funnel, and the contents are shaken. The layers are separated and the aqueous layer is extracted with CH$_2$Cl$_2$ (3×10 mL). The combined organics are washed with brine (1×5 mL), then dried with MgSO$_4$. The MgSO$_4$ is removed by filtration, and the solvents are removed under reduced pressure to give the crude product which is purified by ISCO (12 g column, 0-10% MeOH in CH$_2$Cl$_2$) to give 7 (484 mg/88%). $^1$H NMR (500 MHz, DMSO D$_6$) δ 8.8 (s, 1H), 6.54 (d, J=7.5 Hz), 6.44 (d, J=8.0 Hz, 1H), 4.67 (d, J=4.1 Hz, 1H), 3.78 (m, 2H); LC/MS 377 (M+H$^+$).

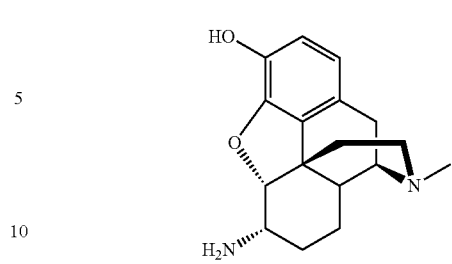

8

Benzyl protected amine 8 (508 mg/1.35 mmol) is dissolved in methanol (10 mL) followed by degassing by sparging with argon for 10 minutes. Pd/C (102 mg) and ammonium formate (483 mg/7.7 mmol) are then added, and the resulting solution is stirred at 70° C. for 1.5 hours. The solution is then filtered over Celite and the solvents are removed under reduced pressure. The resulting crude product is placed under high vacuum overnight. The crude product is analyzed and used without further purification in the next step. $^1$H NMR (500 MHz, CDCl$_3$) δ 6.67 (d, J=8.0 Hz, 1H), 6.53 (d, J=8 Hz, 1H), 4.63 (d, J=4.0 Hz, 1H); LC/MS 287 (M+H$^+$).

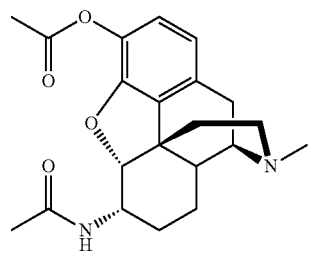

9

Amine 8 is dissolved in CH$_2$Cl$_2$ (anhydrous, 20 mL) under argon followed by the addition of acetic anhydride (433 μL/4.58 mmol) and NEt$_3$ (979 μL/7.0 mmol) at room temperature. The resulting solution is stirred overnight at room temperature under argon. After this time period, the reaction is transferred to a separatory funnel, and the reaction flask is washed with CH$_2$Cl$_2$ (3×10 mL). Additional CH$_2$Cl$_2$ (25 mL) is added to the separatory funnel, followed by the addition of 5% aqueous NaHCO$_3$ (15 mL). The funnel is shaken, and the layers are separated. The aqueous layer is extracted with CH$_2$Cl$_2$ (2×25 mL). The combined organic layers are then washed with water and brine (1×10 mL each) and dried with MgSO$_4$. The organic phase is then filtered and the solvents are removed under reduced pressure. The resulting solid is purified by ISCO (0 to 10% MeOH containing 0.1% concentrated NH$_4$OH, 24 g column) to give the pure product as a white solid (595 mg/80%). $^1$H NMR (500 MHz, DMSO D$_6$) δ 7.30 (d, J=7.5 Hz, 1H), 6.84 (d, J=8.0 Hz, 1H), 6.67 (d, J=8.0 Hz, 1H), 4.63 (d, J=4.0 Hz, 1H), 3.94 (m, 1H); LC/MS 371 (M+H$^+$).

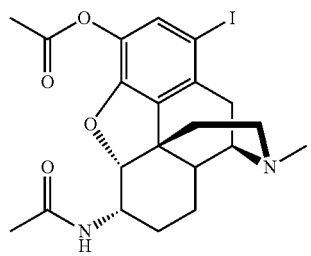

10

6-Acetamide 9 is dissolved in 100 mM aqueous TFA (35 mL), followed by the addition of NIS (230 mg/1.02 mmol) in one portion, and the resulting solution is stirred at room temperature for two hours. After this time period, additional NIS (50 mg/0.22 mmol) is added, and the solution is stirred at room temperature for two hours. The reaction is then transferred to a separatory funnel, and of $CH_2Cl_2$ (50 mL) is added, followed by 5% aq. $NaHCO_3$ (15 mL). The funnel is shaken, and the layers are separated. The aqueous layer is then extracted with $CH_2Cl_2$ (3×25 mL), and the combined organics are washed with 2% sodium bisulfite (2×10 mL). The organic layer is dried with $MgSO_4$, then filtered and the solvents removed under reduced pressure to yield the crude product. The crude product is purified by ISCO (24 g column, 0-10% MeOH in $CH_2Cl_2$) to give 10 as a yellow solid (396 mg/81% yield). $^1$H NMR (500 MHz, DMSO $D_6$) δ 7.39 (d, J=7.5 Hz, 1H), 7.35 (s, 1H), 4.66 (d, J=4.0 Hz, 1H), 3.97 (m, 1H); LC/MS 497 (M+H$^+$).

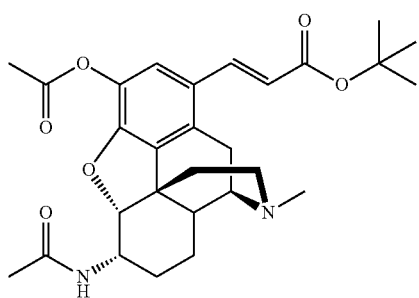

11

DMF (anhydrous, 11 mL) is added to a vial containing iodide 10 (380 mg/0.76 mmol), and the solution is sparged with argon for 5 minutes before the addition of of bis (triphenylphosphine)palladium(II) dichloride (Pd(PPh$_3$)$_2$Cl$_2$) (54 mg/0.08 mmol), tert-butyl-acrylate (0.53 mL/3.65 mmol) and NEt$_3$ (0.42 mL/3.0 mmol). The resulting solution is heated to 90° C. for 6 hours, then cooled to room temperature. The reaction is then transferred to a separatory funnel and the reaction vial washed with CHCl$_3$ (10 mL). Additional CHCl$_3$ (20 mL) is added to the separatory funnel, followed by 5% NaHCO$_3$ (10 mL). The funnel is shaken and the layers are separated. The aqueous phase is extracted with CHCl$_3$ (2×15 mL), and the combined organics are washed with brine (1×10 mL) before drying with MgSO$_4$, filtration, and removal of the solvent under reduced pressure. The crude product is purified by ISCO (24 g column, 0 to 10% MeOH in CH$_2$Cl$_2$) to give 11 as an orange foam (357 mg/92%). $^1$H NMR (500 MHz, DMSO D$_6$) δ 7.67 (d, J=15.0 Hz, 1H), 7.45 (s, 1H), 7.40 (d, J=5 Hz, 1H), 6.30 (d, J=15.0 Hz, 1H), 4.70 (d, J=5 Hz, 1H), 3.98 (m, 1H), 1.47 (s, 9H); LC/MS 498 (M+H$^+$).

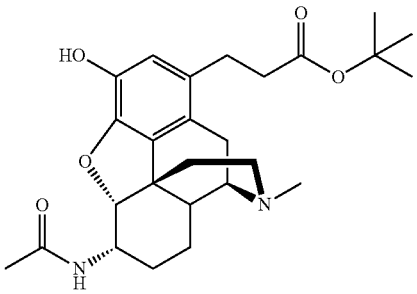

12

Enoate 11 (217 mg/0.44 mmol) is dissolved in MeOH (11 mL, anhydrous) in a 40 mL Thomson vial under argon, followed by the addition of Mg turnings (108 mg/4.44 mmol, oven dried at 130° C. for 2 hours, then allowed to cool in a dessicator) in one portion. The resulting solution is stirred under argon at room temperature for five hours, followed by the addition of Mg turnings (20 mg/0.08 mmol), and then stirred at room temperature for two hours. After this time period, the solvent is removed under reduced pressure, followed by the addition of CHCl$_3$ (10 mL) and brine (10 mL). The resulting emulsion is filtered over sand, first by washing with CHCl$_3$ (50 mL), then with CHCl$_3$:MeOH (6:4, 200 mL). The filtrate is placed into a separatory funnel, and the aqueous and organic phases are separated. The aqueous phase is extracted with CHCl$_3$ (2×15 mL), and the combined organics are dried with MgSO$_4$, filtered, and the solvents removed under reduced pressure. The crude product is purified by ISCO (0-10% MeOH+0.1% concentrated NH$_4$OH in CH$_2$Cl$_2$) to give 12. $^1$H NMR (500 MHz, DMSO D$_6$) δ 8.95 (s, 1H), 7.50 (d, J=7.5 Hz, 1H), 6.50 (s, 1H), 4.57 (m, 1H), 3.94 (m, 1H), 1.36 (s, 9H); LC/MS 457 (M+H$^+$).

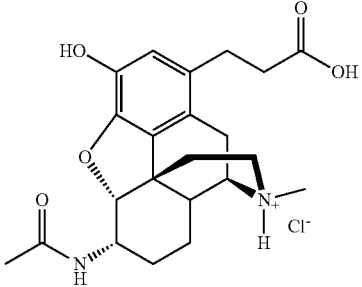

13

CH$_2$Cl$_2$ (6 mL) is added to ester 12 (200 mg/0.44 mmol). The resulting suspension is sonicated, followed by the addition of a solution of TFA:CH$_2$Cl$_2$ (3 mL:1.5 mL), and the suspension became homogeneous followed by becoming cloudy after 5 minutes. The cloudy solution is then stirred at room temperature for 1.5 hours. The solvents are then removed under reduced pressure and the residue is placed under high vacuum for four hours. CH$_2$Cl$_2$ (2 mL) is added to the residue, followed by the addition of HCl in Ether (1 M solution, 550 uL). The solvents are removed under reduced pressure, and the residue is evaporated with CH$_2$Cl$_2$ (2×5 mL). The product 13 is analyzed and used without further purification. ¹H NMR (500 MHz, DMSO D₆) δ 9.12 (s, 1H), 7.52 (d, J=7.5 Hz, 1H), 6.55 (s, 1H), 4.63 (d, J=4.0 Hz, 1H), 3.94 (m, 1H); LC/MS 401 (M+H⁺ of free base).

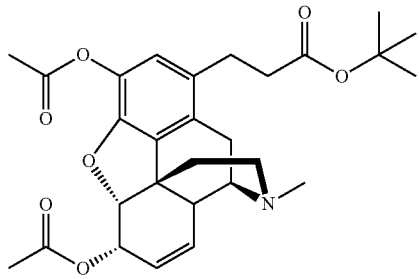

14

To a solution of crude diol 4 (13 mg/0.031 mmol) in CH₂Cl₂ (2 mL, anhydrous) is added acetic anhydride (21 μL/0.21 mmol), NEt₃ (17 μL/0.12 mmol) and DMAP (1 prill), and the resulting solution is stirred overnight at room temperature. The solution is then poured into EtOAc (10 mL), and the organic phase is washed with saturated NaHCO₃ and brine (1×5 mL each). The organic phase is dried with MgSO₄, filtered, and the solvents removed under reduced pressure. The crude product is purified by preparative TLC (9:1 CHCl₃:MeOH) to give 14 as an amorphous solid (4 mg/20% yield). ¹H NMR (500 MHz, DMSO D₆) δ 6.58 (s, 1H), 5.49 (app. q, 2H), 5.09 (m, 1H), 4.99 (d, J=6.5 Hz, 1H), 1.35 (s, 9H); LC/MS 498 (M+H⁺).

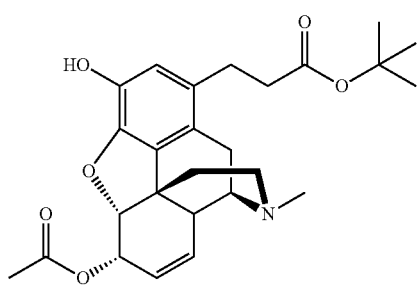

15

Diacetate 14 (75 mg/0.17 mmol) is added to a solution of 50 mM NaPi, pH 7.5 (2 mL):MeOH (2 mL) followed by the addition of hydroxylamine (35 mg/0.50 mmol) in one portion. The resulting solution is stirred at room temperature for four hours, followed by removal of MeOH under reduced pressure. The remaining aqueous solution is extracted with EtOAc (3×8 mL), the combined organics are washed with brine (1×5 mL), dried with MgSO₄, and the solvent removed under reduced pressure. The resulting residue is purified by preparative TLC (9:1 CHCl₃:MeOH) to give 15 as a white solid (67 mg/85%). ¹H NMR (500 MHz, DMSO D₆) δ 9.01 (s, 1H), 6.38 (s, 1H), 5.59 (d, J=9 Hz, 1H), 5.46 (d, J=10 Hz, 1H), 5.12 (m, 1H), 4.98 (d, J=5 Hz, 1H); LC/MS 456 (M+H⁺).

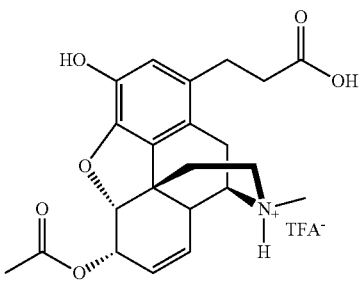

16

6-Acetyl starting material (58 mg/0.13 mmol) is dissolved in 1.5 mL of CH₂Cl₂ followed by the addition of a premixed solution of 1.5 mL of CH₂Cl₂:1.5 mL trifluoroacetic acid (TFA). The resulting solution is stirred at room temperature for one hour. After this time period the solvents are removed under reduced pressure and the remaining residue is placed under high vacuum overnight. The product 16 is used without further purification in the next step (Crude yield: 75 mg/120%). LC/MS 400 (M+H⁺ of free base).

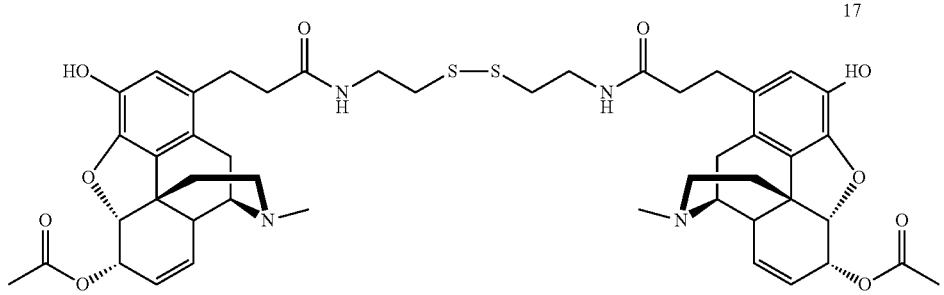

17

To a solution of carboxylic acid 16 (8 mg/0.020 mmol) in CH₂Cl₂:DMF (2 mL:0.8 mL) is added cystamine HCl (2.3 mg/0.01 mmol), HATU (10 mg/0.024 mmol) and DIPEA (14 μL/0.08 mmol). The mixture is bath sonicated until all solids are in solution and then stirred at room temperature overnight. After this time period, solvents are removed under reduced pressure, and the resulting residue is then placed under high vacuum for 4 hours to remove residual DMF. The resulting residue is purified by preparative TLC (iPrOH: NH₄OH:H₂O 10:2:1) to give 17 as a white solid (8 mg/86% yield). ¹H NMR (500 MHz, DMSO D₆) δ 9.10 (s, 1H), 8.03 (t, J=5 Hz, 1H), 6.40 (s, 1H), 5.64 (d, J=10 Hz, 1H), 5.47 (d, J=9.5 Hz, 1H), 5.15 (m, 1H), 5.03 (d, J=6 Hz, 1H), 2.68 (t, J=9.5 Hz, 2H), 2.41 (t, J=7 Hz, 2H); LC/MS 913 (M−H).

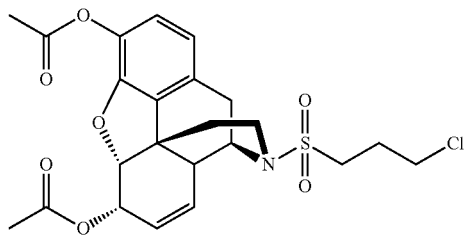

19

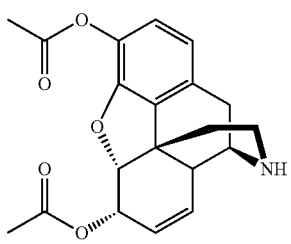

18

Diacetylmorphine (1, 242 mg/0.66 mmol) is added to an oven dried flask equipped with a magnetic stir bar followed by the addition of toluene (6 mL), potassium carbonate (182 mg/1.84 mmol) and trichloroethyl chloroformate (0.36 mL/2.64 mmol) at room temperature. The resulting suspension is then refluxed at 120° C. for 20 hours. After this time period, LC/MS indicated starting material remained. The solution is then cooled to room temp, additional trichloroethyl chloroformate is added (0.20 mL/1.47 mmol), and the solution is refluxed at 120° C. for 8 hours. After this time period the reaction is complete, as monitored by LC/MS. Potassium carbonate is then removed by filtration and toluene is removed under reduced pressure. To the resulting residue is added THF (0.20 mL) and 90% acetic acid (0.105 mL), and the suspension is stirred at room temperature for 6 hours, after which time the reaction is complete as monitored by LC/MS. The solution is separated from the majority of the solid Zn by pipette, and filtered through coarse filter paper into a separatory funnel. The filter paper is washed with isopropanol (5 mL), CHCl₃ (40 mL) and H₂O (20 mL). The aqueous layer is saturated with NaCl, followed by the addition of 50% aqueous NH₂OH dropwise until the pH of the solution reached approximately 7 (pH paper). During this time the funnel is shaken periodically to promote extraction of 18 into the organic phase. CHCl₃ is then separated, and a new portion of CHCl₃ (20 mL) is added before the pH of the solution is adjusted to approximately 9 using 50% aqueous NH₂OH. The separatory funnel is shaken during the pH adjustment periodically. The organic layer is separated, and the resulting aqueous solution is extracted with CHCl₃ (3×15 mL). The combined organic layers are dried with MgSO₄, and the solvents removed under reduced pressure to yield the crude product as a yellow oil (233 mg/100% crude yield); LC/MS 356 (M+H⁺). The crude product is used in the next step without further purification.

Nordiacetylmorphine (18) (65 mg/0.18 mmol) is dissolved in anhydrous CH₂Cl₂ (3 mL), and the solution is cooled to 0° C., followed by the addition of DIPEA (0.063 mL/0.36 mmol) and 3-chloropropylsulfonyl chloride (0.024 mL/0.20 mmol) at 0° C. The reaction is stirred at 0° C. for one hour, then allowed to warm to room temperature with stirring overnight. H₂O (4 mL) and EtOAc (10 mL) are then added. The layers are separated, and the aqueous layer is extracted with EtOAc (2×5 mL). The combined organic layers are washed with H₂O (1×5 mL) and brine (1×5 mL), dried over MgSO₄ and the solvent removed under reduced pressure. The crude product is purified by preparative TLC (1:2 Hexanes:EtOAc) to give 19 as an amorphous solid (40 mg/44% yield). ¹H NMR (500 MHz, CDCl₃) δ 6.82 (d, J=8.2 Hz, 1H), 6.62 (d, J=8.2 Hz, 1H), 5.71 (d, J=11.4 Hz, 1H), 5.42 (d, J=10.3 Hz, 1H), 3.71 (t, J=5.9 Hz, 2H), 2.28 (s, 3H), 2.14 (s, 3H); LC/MS 495 (M−H).

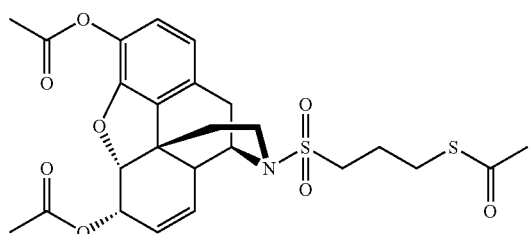

20

Chloride 19 (128 mg/0.26 mmol) is dissolved in anhydrous DMF (4 mL) followed by the addition of potassium thioacetate (148 mg/1.30 mmol), and the solution is heated to 90° C. for 5 hours. The reaction is cooled to room temperature, EtOAc (15 mL) is added, and the solution is transferred to a separatory funnel. The organic phase is washed with H₂O (1×5 mL) and brine (2×5 mL), dried with MgSO₄ and the solvents removed under reduced pressure to yield the crude product which is purified by ISCO (20:1 Hexanes:EtOAc to 5:1 Hexanes:EtOAc) to give thioacetate 20 as an amorphous solid (85 mg/62% yield). ¹H NMR (500 MHz, CDCl₃) δ 6.81 (d, J=9.6 Hz, 1H), 6.61 (d, J=8.3 Hz, 1H), 5.71 (d, J=10.0 Hz, 1H), 5.42 (d, J=10.1 Hz, 1H), 3.06 (t, J=7.1 Hz, 2H), 2.36 (s, 3H), 2.28 (s, 3H); LC/MS 534 (M−H).

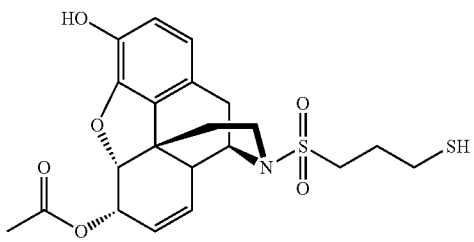

21

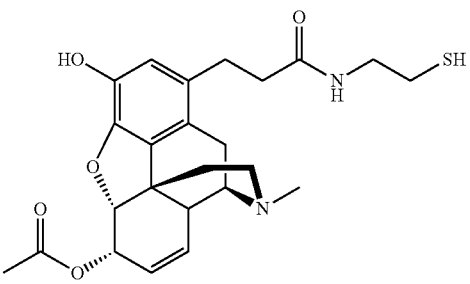

23

Thioacetate 20 (29 mg/0.054 mmol) is dissolved in CH₃OH/THF (2 mL:0.6 mL), followed by the addition of 100 mM sodium phosphate buffer (pH 7.0). 15 mg of hydroxylamine hydrochloride is then added, and the resulting solution is stirred overnight at room temperature. The contents of the vial are transferred to a separatory funnel, EtOAc (10 mL) and water (5 mL) are added, and the funnel is shaken. The layers are separated, and the aqueous layer is extracted with EtOAc (1×5 mL). The combined organic layers are washed with brine (1×5 mL), dried with MgSO₄ and the solvent removed under reduced pressure. The crude product is purified by preparative HPLC to give the pure product as the disulfide derivative of 21 (LC/MS) (2.6 mg/10% yield). Free thiol 21 is obtained by dissolving the disulfide in DMSO:sodium phosphate buffer (pH 7.5) (400 uL DMSO:440 uL 50 mM NaPi), followed by the addition of TCEP (2.2 mg/0.008 mmol) in one portion. The resulting solution is stirred at room temperature for 30 minutes to yield 21. LC/MS 452 (M−H).

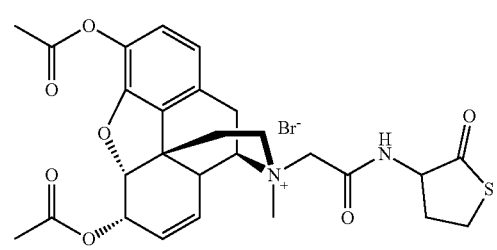

22

Diacetylmorphine 1 (10 mg, 0.03 mmol) is dissolved in acetonitrile (1 mL). To the mixture is added 2-bromo-N-acetyl-HCTL (16 mg, 0.067 mmol). The reaction mixture is then heated at 60° C. for overnight. After overnight, the reaction mixture is cooled down to room temperature. The mixture is then purified using silica TLC plate, eluted with 10% MeOH/DCM to afford 3.6 mg (22%) of 22 as a white powder. ¹H NMR (DMSO-d6) δ 9.14 (1H, d), 6.88 (1H, d), 6.71 (1H, d), 5.65 (1H, d), 5.53 (1H, d); LC/MS 528 (M+).

Conjugation Chemistries: Preparation of Conjugates of 6-Acetyl Morphine (6AM)

A 6-AM derivative 23 having a linking group containing a sulfhydryl group reactive with maleimide or haloacetyl or haloacetamido moiety: may be used to prepare conjugates to a latex solid phase and to KLH as described below.

Bovine serum albumin ("BSA") and polystyrene latex particles (Interfacial Dynamics) are incubated at 25° C. for 30 minutes at 1-10 mg BSA per mL of latex slurry at 1-10% solids in 25 mM citrate buffer, pH approximately 4. The solution is then brought to approximately neutral pH with 150 mM potassium phosphate/30 mM potassium borate, and incubated for an additional 2 hours at 25° C. The suspension is washed three times by resuspension in 50 mM potassium phosphate/10 mM potassium borate/150 mM sodium chloride at approximately neutral pH followed by centrifugation.

An N-hydroxysuccinimide/maleimide bifunctional poly (ethylene glycol) crosslinker as described in U.S. Pat. No. 6,887,952 is added at 5-500 mg/mL in deionized water to the BSA-latex particles at 1-10% solids. The crosslinker is incubated with the BSA-latex particles at room temperature for 2 hours. Excess crosslinker is removed by centrifugation and resuspension in PBS of the now maleimide-functionalized BSA-latex particles.

The derivative (4-8 mg) is dissolved in 0.8 mL DMF-water solution (70:30 v/v) and 200 μL of 1 M KOH, and is incubated for 10 minutes at room temperature. Then the excess of the base is neutralized with a phosphate/hydrochloric acid buffer to pH 7. Maleimide-functionalized BSA-latex particles are added to the solution containing the 6-AM derivative in the presence of 0.1 mM EDTA, and the mixture is incubated at room temperature overnight. KOH is added to maintain the pH at about 7.0. The reaction is stopped in two steps. First by addition of 0.2 mM β-mercaptoethanol and incubation for 30 at room temperature and then by addition of 6 mM N-(hydroxyethyl)maleimide and additional incubation for 30 minutes at room temperature. The 6-AM derivative-conjugated latex particles are purified by centrifugation and resuspension in PBS.

Keyhole Limpet Hemocyanin (KLH, Calbiochem #374817, 50 mg/mL in glycerol) is passed through a 40 mL GH25 column equilibrated in 0.1M potassium phosphate, 0.1M borate, 0.15M sodium chloride buffer, pH 7.5 to remove glycerol. A 1.5-fold molar excess of N-ethylmaleimide is added, and the mixture incubated 30 minutes at room temperature. A 200-fold molar excess of sulfo-SMCC (Pierce #22322) from a 50 mM stock in distilled water is added while vortexing. Vortexing is continued for another 30 seconds, followed by incubation for 10 minutes at room temperature. A 100-fold molar excess of SMCC (Pierce #22360) from an 80 mM stock in acetonitrile is added while vortexing. 1M KOH is added to maintain a pH of between 7.2 and 7.4. The mixture is stirred at room temperature for 90 minutes. After 90 minutes incubation, KLH-SMCC is purified by gel filtration using a GH25 column equilibrated in 0.1M potassium phosphate, 0.02M borate, 0.15M sodium chloride buffer, pH 7.0.

The 6-AM derivative (4-8 mg) is dissolved in 0.8 mL DMF-water solution (70:30 v/v) and 200 µL of 1 M KOH, and is incubated for 10 minutes at room temperature. The excess of the base is neutralized with a phosphate/hydrochloric acid buffer and pH brought to 7. Then, a 2-fold molar excess of derivative (based on the concentration of SMCC in a particular batch of KLH-SMCC) is added to KLH-SMCC, and the mixture stirred for 90 minutes at room temperature. Conjugates are purified by exhaustive dialysis in PBS.

Preparation of Antibodies Against 6-Acetyl Morphine (6AM)

Following immunization with the KLH-conjugated derivative, phage display antibody libraries may be constructed and enriched using biotin-conjugated 24 and magnetic streptavidin latex as generally described in U.S. Pat. No. 6,057,098. The antibody phage library is selected with 24, transferred into a plasmid expression vector and electroporated into bacterial cells. Simultaneous negative selection is performed with 25, 26, and 27 to select against antibodies binding to undesired epitopes.

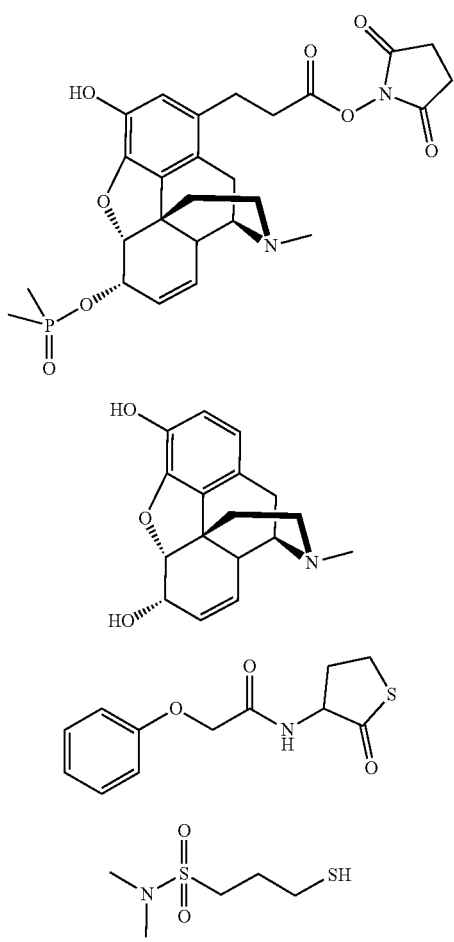

The bacterial cells from each antibody library are streaked on agar to generate colonies. The colonies, coding for monoclonal antibodies, are used to inoculate culture medium in individual wells in 96-well plates. The liquid cultures are grown overnight and used to generate frozen cell stocks. The frozen cell stocks are used to generate duplicate 96-well plate cultures, followed by expression and purification of the monoclonal antibodies in soluble form in microgram quantities. A competitive assay for 6-AM developed with a selected antibody exhibited no crossreactivity with morphine, morphine-3-glucuronide, or morphine-6-glucuronide at clinically relevant concentrations.

Evaluation of Cross-Reactivity of Antibodies Against 6-Acetyl Morphine (6AM) with Other Heroin Metabolites Cross reactivity to heroin metabolites and other common structurally related opiates may be evaluated using the antibodies described herein. Immunoassays are constructed using the antibodies of Example 3, configured to operate in a competitive mode immunoassay format, in which the analogue compounds of the invention are compared with other related compounds for cross reaction against 6-acetylmorphine. Labeled 6-acetylmorphine conjugates are prepared for use as the detectable species. Aliquots of labeled 6-acetylmorphine at 10 ng/mL are incubated in the presence of competing compound with the antibody of the invention, and the level of interaction of the competitor compound determined as a reduction in measured signal compared with the situation where only 6-acetylmorphine is present. The results are provided in the Table 1. The data demonstrate the high specificity of the antibody for 6-acetylmorphine. With many of the competing species being applied at an excess of 100,000 to 1 over 6-acetylmorphine; there is no detectable cross reaction; and with 6-acetylcodeine at a 30:1 excess over 6-acetylmorphone there is only a 3% cross reaction. The data clearly indicate the specificity of the antibodies of the invention for 6-acetylmorphine.

EXAMPLES

The following examples serve to illustrate the present invention. These examples are in no way intended to limit the scope of the invention.

Example 1: 6-Acetyl Morphine (6AM) Derivatives at the 1-Position of the A Ring in the Morphine Scaffold The synthetic schemes are shown below and depicted in FIGS. 2-6. For the synthesis of 6-phosphinyl derivative 6, morphine sulfate was acetylated to make diacetylmorphine, followed by iodination to yield 1-Iodo-diacetylmorphine derivative 2. Heck coupling of 2 with tert-butyl acrylate yielded enoate 3, which was selectively reduced using MgO/MeOH to give saturated diol 4. Phosphinylation of 4, followed by removal of the aryl Phosphinyl yielded 5, which was deprotected using acidic conditions to yield the 6-phosphinyl derivative 6 (FIG. 2). For the synthesis of 6-acetamide derivative 13, hydromorphine hydrochloride was exposed to reductive amination with benzylamine, followed by reduction to yield 6-aminohydromorphine derivative 8. The 6-amino compound was acetylated, followed by iodination to yield 1-iodo-6-acetamide 10. Heck coupling of 10 with tert-butyl acrylate yielded enoate 11, which was reduced using MgO/MeOH to give saturated 6-acetamide 12. Acidic deprotection of 12 gave 6-acetamide derivative 13 (FIG. 3). For the synthesis of 6-acetyl disulfide 17, saturated diol 4 was acetylated to give 14, followed by removal of the phenolic acetate with hydroxylamine to yield 15, and deprotection of the tert-butyl ester using acidic conditions to give carboxylic acid 16. Carboxylic acid 16 was then coupled with cystamine to give 6-acetyl disulfide 17 (FIG. 4). For the synthesis of sulfonamide 21, diacetylmorphine was N-demethylated to nor-diacetylmorphine 18, followed by formation of chloride 19. The chloride was displaced to yield thioacetate 20, which was deprotected to give sulfonamide 21 (FIG. 5). For the synthesis of quaternary salt 22, diacetylmorphine 1 was N-alkylated with 2-bromo-N-acetyl-HCTL (FIG. 6).

General Methods

All starting materials and solvents were obtained from commercial vendors unless otherwise noted. Morphine sulfate pentahydrate and Hydromorphone hydrochloride were obtained from Spectrum Chemical Company. $^1$H NMR spectra were taken in DMSO $D_6$ (from ampoules) or $CDCl_3$ at 500 MHz by NuMega Laboratories. HPLC was conducted using an Agilent Model 1200 machine equipped with either a Waters X-bridge (C18, 3.5 μm, 3.0×50 μm) or Fisher Thermo Hypercarb (5.0 um, 4.6×100 mm) columns. For HPLC, solvent A was 95% $H_2O$/5% $CH_3CN$/0.1% TFA, solvent B was 95% $CH_3CN$/5% $H_2O$/0.1% TFA. HPLC runs were either 6 or 15 minutes long. For the 6 minute run: 0 minutes, 5% B, 0-5 minutes, gradient to 100% B, 5-6 minutes, gradient to 5% B; for the 15 minute run: 0 minutes 0% B, 0-12 minutes, gradient to 100% B, 12-14 minutes 100% B, 14-15 minutes, gradient to 0% B. LC/MS was conducted using a Waters model e2795 series LC equipped with a model 2996 photodiode array detector, a series 3100 MS and a Waters X-Bridge-C18 column, 3.5 um, 2.1×50 mm. For LC/MS, solvent A was 95% $H_2O$/5% $CH_3CN$/0.1% Formic Acid; solvent B was 95% $CH_3CN$/5% $H_2O$/0.1% Formic Acid. HPLC runs were 5 minutes: 0 minutes 0% B, 0-3.5 minutes, gradient to 100% B, 3.5-4.8 minutes 100% B, 4.8 to 4.9 minutes gradient to 0% B, 5.0 minutes, 0% B.

Synthetic Procedures

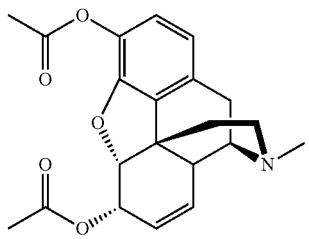

Diacetylmorphine (1): Morphine sulfate pentahydrate (1 g/1.32 mmol morphine sulfate pentahydrate/2.64 mmol morphine) was suspended in $CH_2Cl_2$ (10 mL) followed by the addition of $NEt_3$ (2.0 mL/14 mmol), pyridine (3 mL) and acetic anhydride (2.4 mL/25.4 mmol). The resulting suspension was stirred at room temperature for one hour, during which time all morphine sulfate went into solution. The solution was then stirred for 14 hours at room temperature. After this time period, additional acetic anhydride (200 μL/2.1 mmol) was added, and the solution was heated to 40° C. for 6 hours. The solution was then cooled to room temperature, MeOH (7 mL) was added, and the resulting solution stirred at room temperature for one hour before removal of the solvents under reduced pressure. The remaining residue was partitioned in a separatory funnel between EtOAc (90 mL) and saturated $NaHCO_3$ (45 mL), and the biphasic mixture shaken until a minimum amount of gas was discharged. The organic phase was washed with saturated $NaHCO_3$ (20 mL) and brine (20 mL) and dried with $MgSO_4$. The solvents were evaporated, and the resulting light brown residue placed under high vacuum overnight to afford diacetylmorphine (905 mg/70% yield). $^1$H NMR (500 MHz, DMSO $D_6$) δ 6.77 (d, J=8.5 Hz, 1H), 6.63 (d, J=8.0 Hz, 1H), 5.57 (m, 1H), 5.48 (m, 1H), 5.11 (m, 1H), 5.08 (m, 1H); LC/MS 370 (M+H$^+$).

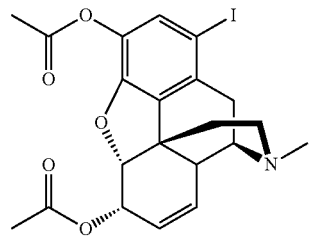

1-Iododiacetylmorphine (2): N-Iodosuccinimide (NIS) (427 mg/1.9 mmol) was added in one portion to a solution of 1 (460 mg/1.25 mmol) in 0.05 M $H_2SO_4$ (15 mL), and the resulting solution was stirred at room temperature for three hours before the addition of NIS (93 mg/0.4 mmol) in one portion. The reaction was then stirred at room temperature for three hours, after which time LC/MS indicated the reaction was complete. The reaction was then transferred to a separatory funnel containing 30 mL of EtOAc and the reaction vessel was washed well with EtOAc. Saturated $NaHCO_3$ (20 mL) was then added and the separatory funnel was shaken. The layers were separated, and the aqueous layer was extracted with EtOAc (2×15 mL). The combined organics were washed with 2% sodium bisulfite (2×10 mL) and brine (1×10 ml), dried with $MgSO_4$, and the solvents removed under reduced pressure. The crude product was purified by ISCO (24 g column, 0-10% MeOH in $CH_2Cl_2$) to afford the pure product as a yellow solid (618 mg/94% yield). $^1$H NMR (500 MHz, DMSO $D_6$) δ 7.27 (s, 1H), 5.53 (app. q, 2H), 5.14 (m, 1H), 5.06 (d, J=6.5 Hz, 1H); LC/MS 496 (M+H$^+$).

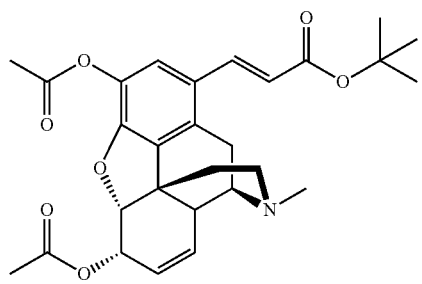

Anhydrous DMF (25 mL) was added to a vial containing 2 (1.19 g/2.4 mmol), and the solution was sparged with argon for 5 minutes, followed by the addition of bis(triphenylphosphine)palladium(II) dichloride (Pd(PPh$_3$)$_2$Cl$_2$) (0.17 g/0.24 mmol), tert-butyl acrylate (1.7 mL/11.7 mmol) and NEt$_3$ (1.3 mL/9.4 mmol). The resulting solution was heated to 90° C. for 6 hours, then cooled to room temperature. EtOAc (50 mL) was added, and the solution was transferred to a separatory funnel. The organic layer was washed with saturated aq NaHCO$_3$ (1×15 mL), and the aqueous layer was back extracted with EtOAc (2×15 mL). The combined organics were washed with brine (1×15 mL), dried with MgSO$_4$ and the solvent removed under reduced pressure. The crude product was purified by ISCO (24 g column, 0-10% MeOH in CH$_2$Cl$_2$) to afford enoate 3 as a yellow solid (795 mg/67% yield). $^1$H NMR (500 MHz, DMSO D$_6$) δ 7.62 (d, J=16 Hz, 1H), 7.35 (s, 1H), 6.27 (d, J=16 Hz, 1H), 5.52 (app. q, 2H), 5.14 (m, 1H), 5.10 (d, J=7 Hz, 1H), 1.47 (s, 9H); LC/MS 496 (M+H$^+$).

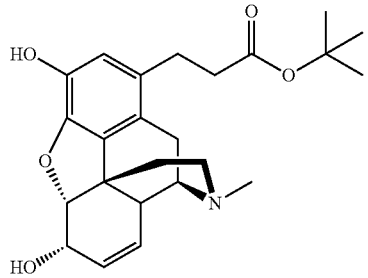

4

Enoate 3 (828 mg/1.67 mmol) was dissolved in MeOH (12 mL, Sigma-Aldrich, anhydrous), followed by the addition of magnesium turnings (280 mg/11.5 mmol) and the resulting solution was stirred at room temperature for 2 hours, after which time all Mg had dissolved. Additional Mg turnings were added (50 mg/2.1 mmol), and the reaction was stirred for 2 hours. The solvent was then removed under reduced pressure to yield a dark brown solid, which was dissolved in 10 mL of CHCl$_3$ (bath sonication was necessary to dissolve), and the solution was transferred to a 500 mL separatory funnel. The reaction vial was washed with CHCl$_3$ (3×10 mL), and 20 mL of CHCl$_3$ was added to the separatory funnel, followed by the addition of 15 mL of brine. Upon the addition of brine, an emulsion was formed. An additional 30 mL of CHCl$_3$ was added to the funnel, and the suspension was separated by draining the organic phase into a 1 L Erlenmeyer flask. The remaining aqueous layer was extracted with CHCl$_3$ (6×35 mL), and the combined organic phases were dried overnight by stirring with 37 g of sodium sulfate. After overnight stirring, the organic phase was cloudy. The solution was filtered over celite. The celite was washed with CHCl$_3$ (3×40 mL), and the solvents were evaporated to obtain 4 as an amorphous solid (230 mg/33% yield) that was used without further purification in the next step. LC/MS 414 (M+H$^+$).

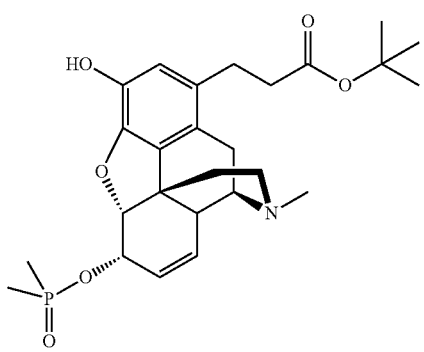

5

Dimethylphosphinyl chloride was added in one portion to an oven dried 250 mL round bottom flask, followed by the addition of pyridine (anhydrous, 5 mL), and the resulting solution was cooled to 0° C. in an ice bath for 30 minutes before the addition of tetrazole (16 mL of a 3% by mass solution in CH$_3$CN) in one portion. The resulting solution was stirred at 0° C. for 10 minutes before the addition of a solution of diol (crude Mg reduction material 4 was) in pyridine (anhydrous, 5 mL) at the same temperature. The solution was stirred at 0° C. for 10 minutes, followed by removal of the ice bath and allowed to warm to room temperature for two hours. After this time period, LC MS indicated the reaction was complete, only the mass of the diphosphinyl product was observed. Pyridine solvent was then removed under reduced pressure (residual pyridine was present). After removal of most of the pyridine, 30 mL of saturated NaHCO$_3$ was added, followed by 15 mL of MeOH. The resulting solution was stirred at room temperature for 48 hours. The solution was transferred to a 250 mL separatory funnel, and the reaction flask was washed with CH$_2$Cl$_2$ (2×15 mL). 20 mL of CH$_2$Cl$_2$ was added to the separatory funnel, followed by 10 mL of brine. The funnel was gently shaken, and the organic layer was separated. The aqueous layer was extracted with CH$_2$Cl$_2$ (3×20 mL), the combined organic layers were dried with MgSO$_4$ and the solvents were removed under reduced pressure, The product was purified by ISCO using a 24 g silica column (100% CH$_2$Cl$_2$ to 80% CH$_2$Cl$_2$:20% CH$_2$Cl$_2$:MeOH:concentrated NH$_4$OH (8:2:0.001) to afford 5 (176 mg/65% from crude 4). $^1$H NMR (500 MHz, DMSO D$_6$) δ 8.81 (s, 1H), 6.32 (s, 1H), 5.55 (d, J=10 Hz, 1H), 5.38 (d, J=10 Hz, 1H), 4.83 (m, 1H), 4.77 (d, J=5 Hz, 1H), 1.55-1.44 (dd, J=15, 40 Hz, 6H), 1.37 (s, 9H); LC/MS 491 (M+H$^+$).

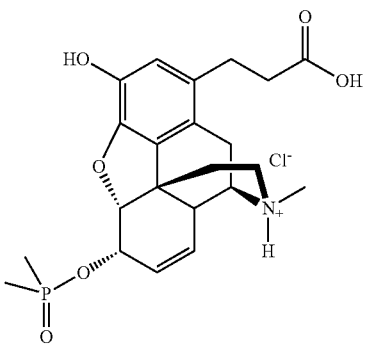

6

Tert-butyl ester 5 (171 mg/0.35 mmol) was dissolved in CH$_2$Cl$_2$ (3 mL) followed by the addition of TFA:CH$_2$Cl$_2$ (3 mL:1 mL). The resulting solution was stirred at room temperature for 2 hours, followed by removal of the solvents were removed under reduced pressure. The residue was then placed under high vacuum for 2 hours. After high vacuum, 1.5 mL of CH$_2$Cl$_2$ was added, followed by the addition of HCl in ether (450 uL). The solvents were evaporated, and the resulting solid was evaporated with CH$_2$Cl$_2$ (1×3 mL) and CH$_3$CN (2×3 mL), then placed under high vacuum overnight to give 6 as an off-white solid (159 mg/99% yield). $^1$H NMR (500 MHz, DMSO D$_6$) δ 9.10 (s, 1H), 6.44 (s, 1H), 5.69 (d, J=10 Hz, 1H), 5.42 (d, J=10 Hz, 1H), 4.95 (d, J=10 Hz, 1H), 4.86 (m, 1H), 1.57-1.46 (dd, J=15, 40 Hz, 6H); $^{31}$P NMR (125 MHz, CD$_3$OD) δ 60.47; LC/MS 434 (M+H$^+$ of free base).

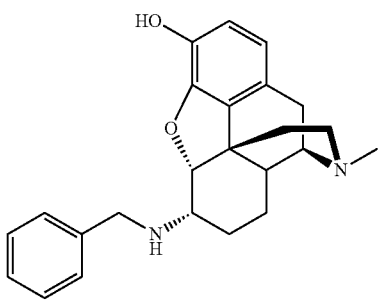

7

To an oven dried flask equipped with a magnetic stir bar was added hydromorphone HCl (469 mg/1.5 mmol) followed by suspending in 1,2-dichloroethane (anhydrous, 12 mL). To the resulting suspension was added benzylamine (192 μL/1.8 mmol) and sodium triacetoxyborohydride (592 mg/2.8 mmol). The resulting suspension was stirred overnight under argon at room temperature. The suspension was then transferred to a separatory funnel, and the reaction vial was washed with $CH_2Cl_2$ (3×10 mL). Saturated $NaHCO_3$ (10 mL) was added to the separatory funnel, and the contents were shaken. The layers were separated and the aqueous layer was extracted with $CH_2Cl_2$ (3×10 mL). The combined organics were washed with brine (1×5 mL), then dried with $MgSO_4$. The $MgSO_4$ was removed by filtration, and the solvents were removed under reduced pressure to give the crude product which was purified by ISCO (12 g column, 0-10% MeOH in $CH_2Cl_2$) to give 7 (484 mg/88%). $^1$H NMR (500 MHz, DMSO $D_6$) δ 8.8 (s, 1H), 6.54 (d, J=7.5 Hz), 6.44 (d, J=8.0 Hz, 1H), 4.67 (d, J=4.1 Hz, 1H), 3.78 (m, 2H); LC/MS 377 (M+H$^+$).

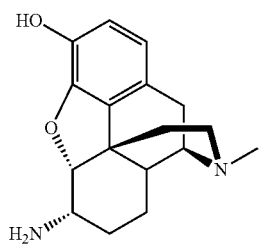

8

Benzyl protected amine 8 (508 mg/1.35 mmol) was dissolved in methanol (10 mL) followed by degassing by sparging with argon for 10 minutes. Pd/C (102 mg) and ammonium formate (483 mg/7.7 mmol) were then added, and the resulting solution was stirred at 70° C. for 1.5 hours. The solution was then filtered over Celite and the solvents were removed under reduced pressure. The resulting crude product was placed under high vacuum overnight. The crude product was analyzed and used without further purification in the next step. $^1$H NMR (500 MHz, CDCl$_3$) δ 6.67 (d, J=8.0 Hz, 1H), 6.53 (d, J=8 Hz, 1H), 4.63 (d, J=4.0 Hz, 1H); LC/MS 287 (M+H$^+$).

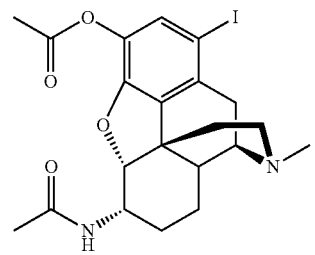

9

Amine 8 was dissolved in $CH_2Cl_2$ (anhydrous, 20 mL) under argon followed by the addition of acetic anhydride (433 μL/4.58 mmol) and NEt$_3$ (979 μL/7.0 mmol) at room temperature. The resulting solution was stirred overnight at room temperature under argon. After this time period, the reaction was transferred to a separatory funnel, and the reaction flask was washed with $CH_2Cl_2$ (3×10 mL). Additional $CH_2Cl_2$ (25 mL) was added to the separatory funnel, followed by the addition of 5% aqueous NaHCO$_3$ (15 mL). The funnel was shaken, and the layers were separated. The aqueous layer was extracted with $CH_2Cl_2$ (2×25 mL). The combined organic layers were then washed with water and brine (1×10 mL each) and dried with MgSO$_4$. The organic phase was then filtered and the solvents were removed under reduced pressure. The resulting solid was purified by ISCO (0 to 10% MeOH containing 0.1% concentrated NH$_4$OH, 24 g column) to give the pure product as a white solid (595 mg/80%). $^1$H NMR (500 MHz, DMSO D$_6$) δ 7.30 (d, J=7.5 Hz, 1H), 6.84 (d, J=8.0 Hz, 1H), 6.67 (d, J=8.0 Hz, 1H), 4.63 (d, J=4.0 Hz, 1H), 3.94 (m, 1H); LC/MS 371 (M+H$^+$).

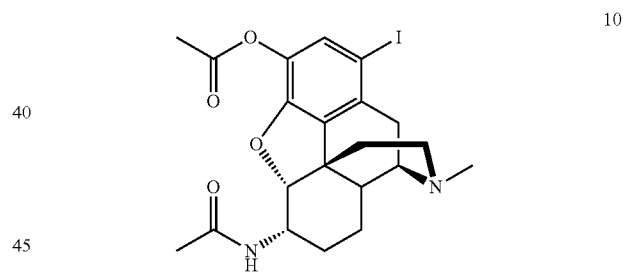

10

6-Acetamide 9 was dissolved in 100 mM aqueous TFA (35 mL), followed by the addition of NIS (230 mg/1.02 mmol) in one portion, and the resulting solution was stirred at room temperature for two hours. After this time period, additional NIS (50 mg/0.22 mmol) was added, and the solution was stirred at room temperature for two hours. The reaction was then transferred to a separatory funnel, and of $CH_2Cl_2$ (50 mL) was added, followed by 5% aq. NaHCO$_3$ (15 mL). The funnel was shaken, and the layers were separated. The aqueous layer was then extracted with $CH_2Cl_2$ (3×25 mL), and the combined organics were washed with 2% sodium bisulfite (2×10 mL). The organic layer was dried with MgSO$_4$, then filtered and the solvents removed under reduced pressure to yield the crude product. The crude product was purified by ISCO (24 g column, 0-10% MeOH in $CH_2Cl_2$) to give 10 as a yellow solid (396 mg/81% yield). $^1$H NMR (500 MHz, DMSO D$_6$) δ 7.39 (d, J=7.5 Hz, 1H), 7.35 (s, 1H), 4.66 (d, J=4.0 Hz, 1H), 3.97 (m, 1H); LC/MS 497 (M+H$^+$).

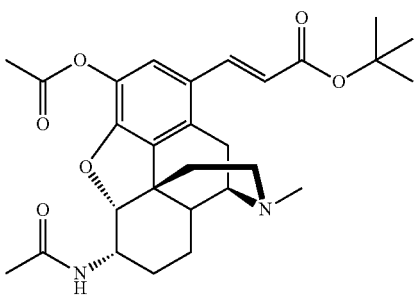

11

DMF (anhydrous, 11 mL) was added to a vial containing iodide 10 (380 mg/0.76 mmol), and the solution was sparged with argon for 5 minutes before the addition of of bis(triphenylphosphine)palladium(II) dichloride (Pd(PPh$_3$)$_2$Cl$_2$) (54 mg/0.08 mmol), tert-butyl-acrylate (0.53 mL/3.65 mmol) and NEt$_3$ (0.42 mL/3.0 mmol). The resulting solution was heated to 90° C. for 6 hours, then cooled to room temperature. The reaction was then transferred to a separatory funnel and the reaction vial washed with CHCl$_3$ (10 mL). Additional CHCl$_3$ (20 mL) was added to the separatory funnel, followed by 5% NaHCO$_3$ (10 mL). The funnel was shaken and the layers were separated. The aqueous phase was extracted with CHCl$_3$ (2×15 mL), and the combined organics were washed with brine (1×10 mL) before drying with MgSO$_4$, filtration, and removal of the solvent under reduced pressure. The crude product was purified by ISCO (24 g column, 0 to 10% MeOH in CH$_2$Cl$_2$) to give 11 as an orange foam (357 mg/92%). $^1$H NMR (500 MHz, DMSO D$_6$) δ 7.67 (d, J=15.0 Hz, 1H), 7.45 (s, 1H), 7.40 (d, J=5 Hz, 1H), 6.30 (d, J=15.0 Hz, 1H), 4.70 (d, J=5 Hz, 1H), 3.98 (m, 1H), 1.47 (s, 9H); LC/MS 498 (M+H$^+$).

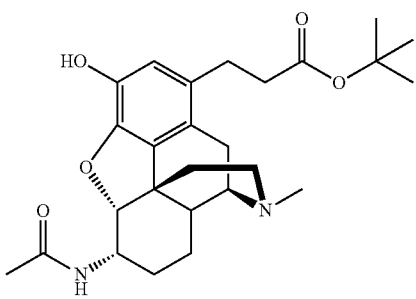

Enoate 11 (217 mg/0.44 mmol) was dissolved in MeOH (11 mL, anhydrous) in a 40 mL Thomson vial under argon, followed by the addition of Mg turnings (108 mg/4.44 mmol, oven dried at 130° C. for 2 hours, then allowed to cool in a dessicator) in one portion. The resulting solution was stirred under argon at room temperature for five hours, followed by the addition of Mg turnings (20 mg/0.08 mmol), and then stirred at room temperature for two hours. After this time period, the solvent was removed under reduced pressure, followed by the addition of CHCl$_3$ (10 mL) and brine (10 mL). The resulting emulsion was filtered over sand, first by washing with CHCl$_3$ (50 mL), then with CHCl$_3$:MeOH (6:4, 200 mL). The filtrate was placed into a separatory funnel, and the aqueous and organic phases were separated. The aqueous phase was extracted with CHCl$_3$ (2×15 mL), and the combined organics were dried with MgSO$_4$, filtered, and the solvents removed under reduced pressure. The crude product was purified by ISCO (0-10% MeOH+0.1% concentrated NH$_4$OH in CH$_2$Cl$_2$) to give 12. $^1$H NMR (500 MHz, DMSO D$_6$) δ 8.95 (s, 1H), 7.50 (d, J=7.5 Hz, 1H), 6.50 (s, 1H), 4.57 (m, 1H), 3.94 (m, 1H), 1.36 (s, 9H); LC/MS 457 (M+H$^+$).

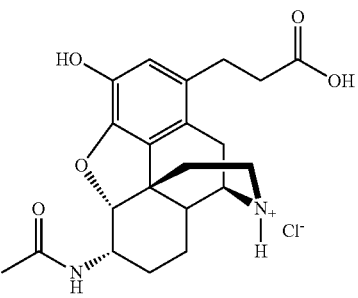

CH$_2$Cl$_2$ (6 mL) was added to ester 12 (200 mg/0.44 mmol). The resulting suspension was sonicated, followed by the addition of a solution of TFA:CH$_2$Cl$_2$ (3 mL:1.5 mL), and the suspension became homogeneous followed by becoming cloudy after 5 minutes. The cloudy solution was then stirred at room temperature for 1.5 hours. The solvents were then removed under reduced pressure and the residue was placed under high vacuum for four hours. CH$_2$Cl$_2$ (2 mL) was added to the residue, followed by the addition of HCl in Ether (1 M solution, 550 uL). The solvents were removed under reduced pressure, and the residue was evaporated with CH$_2$Cl$_2$ (2×5 mL). The product 13 was analyzed and used without further purification. $^1$H NMR (500 MHz, DMSO D$_6$) δ 9.12 (s, 1H), 7.52 (d, J=7.5 Hz, 1H), 6.55 (s, 1H), 4.63 (d, J=4.0 Hz, 1H), 3.94 (m, 1H); LC/MS 401 (M+H$^+$ of free base).

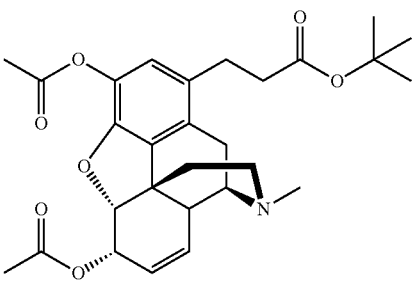

To a solution of crude diol 4 (13 mg/0.031 mmol) in CH$_2$Cl$_2$ (2 mL, anhydrous) was added acetic anhydride (21 μL/0.21 mmol), NEt$_3$ (17 μL/0.12 mmol) and DMAP (1 prill), and the resulting solution was stirred overnight at room temperature. The solution was then poured into EtOAc (10 mL), and the organic phase was washed with saturated NaHCO$_3$ and brine (1×5 mL each). The organic phase was dried with MgSO$_4$, filtered, and the solvents removed under reduced pressure. The crude product was purified by preparative TLC (9:1 CHCl$_3$:MeOH) to give 14 as an amorphous solid (4 mg/20% yield). $^1$H NMR (500 MHz, DMSO D$_6$) δ 6.58 (s, 1H), 5.49 (app. q, 2H), 5.09 (m, 1H), 4.99 (d, J=6.5 Hz, 1H), 1.35 (s, 9H); LC/MS 498 (M+H$^+$).

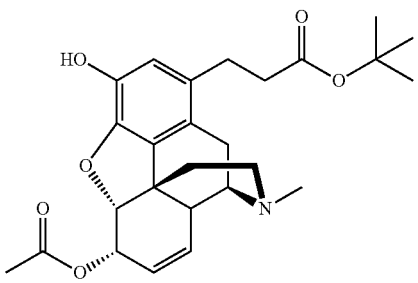

Diacetate 14 (75 mg/0.17 mmol) was added to a solution of 50 mM *NaPi*, pH 7.5 (2 mL):MeOH (2 mL) followed by the addition of hydroxylamine (35 mg/0.50 mmol) in one portion. The resulting solution was stirred at room temperature for four hours, followed by removal of MeOH under reduced pressure. The remaining aqueous solution was extracted with EtOAc (3×8 mL), the combined organics were washed with brine (1×5 mL), dried with $MgSO_4$, and the solvent removed under reduced pressure. The resulting residue was purified by preparative TLC (9:1 $CHCl_3$:MeOH) to give 15 as a white solid (67 mg/85%). $^1$H NMR (500 MHz, DMSO $D_6$) δ 9.01 (s, 1H), 6.38 (s, 1H), 5.59 (d, J=9 Hz, 1H), 5.46 (d, J=10 Hz, 1H), 5.12 (m, 1H), 4.98 (d, J=5 Hz, 1H); LC/MS 456 (M+H$^+$).

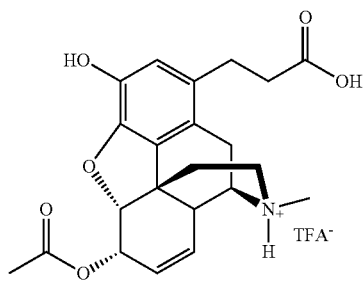

6-Acetyl starting material (58 mg/0.13 mmol) was dissolved in 1.5 mL of $CH_2Cl_2$ followed by the addition of a premixed solution of 1.5 mL of $CH_2Cl_2$:1.5 mL trifluoroacetic acid (TFA). The resulting solution was stirred at room temperature for one hour. After this time period the solvents were removed under reduced pressure and the remaining residue was placed under high vacuum overnight. The product 16 was used without further purification in the next step (Crude yield: 75 mg/120%). LC/MS 400 (M+H$^+$ of free base).

To a solution of carboxylic acid 16 (8 mg/0.020 mmol) in $CH_2Cl_2$:DMF (2 mL:0.8 mL) was added cystamine HCl (2.3 mg/0.01 mmol), HATU (10 mg/0.024 mmol) and DIPEA (14 μL/0.08 mmol). The mixture was bath sonicated until all solids were in solution and then stirred at room temperature overnight. After this time period, solvents were removed under reduced pressure, and the resulting residue was then placed under high vacuum for 4 hours to remove residual DMF. The resulting residue was purified by preparative TLC (iPrOH:$NH_4OH$:$H_2O$ 10:2:1) to give 17 as a white solid (8 mg/86% yield). $^1$H NMR (500 MHz, DMSO $D_6$) δ 9.10 (s, 1H), 8.03 (t, J=5 Hz, 1H), 6.40 (s, 1H), 5.64 (d, J=10 Hz, 1H), 5.47 (d, J=9.5 Hz, 1H), 5.15 (m, 1H), 5.03 (d, J=6 Hz, 1H), 2.68 (t, J=9.5 Hz, 2H), 2.41 (t, J=7 Hz, 2H); LC/MS 913 (M−H).

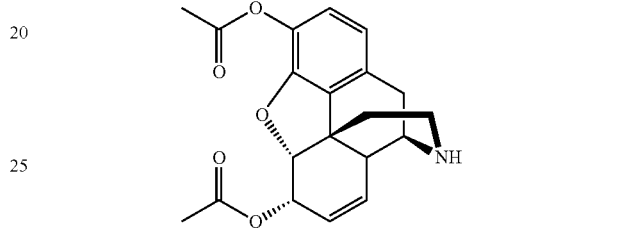

Diacetylmorphine (1, 242 mg/0.66 mmol) was added to an oven dried flask equipped with a magnetic stir bar followed by the addition of toluene (6 mL), potassium carbonate (182 mg/1.84 mmol) and trichloroethyl chloroformate (0.36 mL/2.64 mmol) at room temperature. The resulting suspension was then refluxed at 120° C. for 20 hours. After this time period, LC/MS indicated starting material remained. The solution was then cooled to room temp, additional trichloroethyl chloroformate was added (0.20 mL/1.47 mmol), and the solution was refluxed at 120° C. for 8 hours. After this time period the reaction was complete, as monitored by LC/MS. Potassium carbonate was then removed by filtration and toluene was removed under reduced pressure. To the resulting residue was added THF (0.20 mL) and 90% acetic acid (0.105 mL), and the suspension was stirred at room temperature for 6 hours, after which time the reaction was complete as monitored by LC/MS. The solution was separated from the majority of the solid Zn by pipette, and filtered through coarse filter paper into a separatory funnel. The filter paper was washed with isopropanol (5 mL), $CHCl_3$ (40 mL) and $H_2O$ (20 mL). The aqueous layer was saturated with NaCl, followed by the addition of 50% aqueous $NH_2OH$ dropwise until the pH of

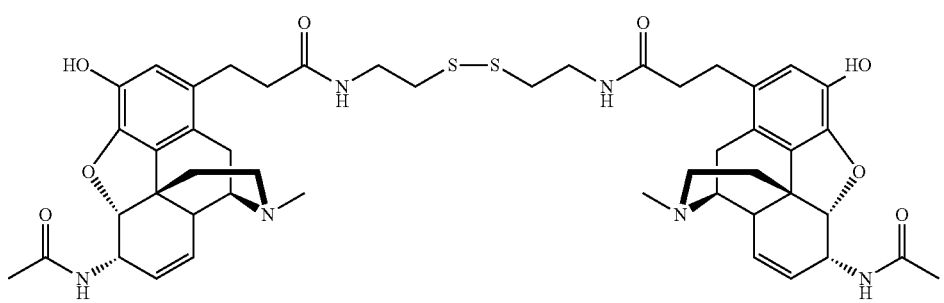

the solution reached approximately 7 (pH paper). During this time the funnel was shaken periodically to promote extraction of 18 into the organic phase. CHCl₃ was then separated, and a new portion of CHCl₃ (20 mL) was added before the pH of the solution was adjusted to approximately 9 using 50% aqueous NH₂OH. The separatory funnel was shaken during the pH adjustment periodically. The organic layer was separated, and the resulting aqueous solution was extracted with CHCl₃ (3×15 mL). The combined organic layers were dried with MgSO₄, and the solvents removed under reduced pressure to yield the crude product as a yellow oil (233 mg/100% crude yield); LC/MS 356 (M+H⁺). The crude product was used in the next step without further purification.

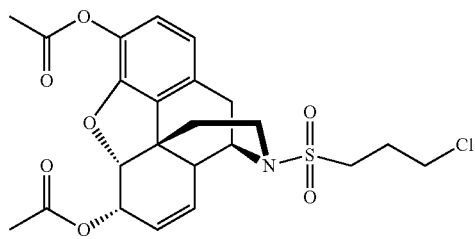

19

Nordiacetylmorphine (18) (65 mg/0.18 mmol) was dissolved in anhydrous CH₂Cl₂ (3 mL), and the solution was cooled to 0° C., followed by the addition of DIPEA (0.063 mL/0.36 mmol) and 3-chloropropylsulfonyl chloride (0.024 mL/0.20 mmol) at 0° C. The reaction was stirred at 0° C. for one hour, then allowed to warm to room temperature with stirring overnight. H₂O (4 mL) and EtOAc (10 mL) were then added. The layers were separated, and the aqueous layer was extracted with EtOAc (2×5 mL). The combined organic layers were washed with H₂O (1×5 mL) and brine (1×5 mL), dried over MgSO₄ and the solvent removed under reduced pressure. The crude product was purified by preparative TLC (1:2 Hexanes:EtOAc) to give 19 as an amorphous solid (40 mg/44% yield). ¹H NMR (500 MHz, CDCl₃) δ 6.82 (d, J=8.2 Hz, 1H), 6.62 (d, J=8.2 Hz, 1H), 5.71 (d, J=11.4 Hz, 1H), 5.42 (d, J=10.3 Hz, 1H), 3.71 (t, J=5.9 Hz, 2H), 2.28 (s, 3H), 2.14 (s, 3H); LC/MS 495 (M−H).

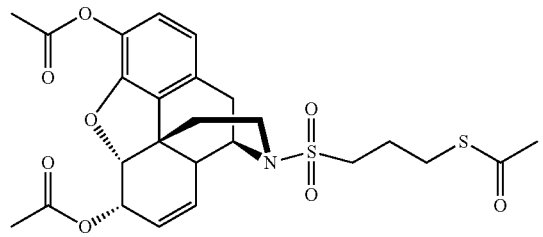

20

Chloride 19 (128 mg/0.26 mmol) was dissolved in anhydrous DMF (4 mL) followed by the addition of potassium thioacetate (148 mg/1.30 mmol), and the solution was heated to 90° C. for 5 hours. The reaction was cooled to room temperature, EtOAc (15 mL) was added, and the solution was transferred to a separatory funnel. The organic phase was washed with H₂O (1×5 mL) and brine (2×5 mL), dried with MgSO₄ and the solvents removed under reduced pressure to yield the crude product which was purified by ISCO (20:1 Hexanes:EtOAc to 5:1 Hexanes:EtOAc) to give thioacetate 20 as an amorphous solid (85 mg/62% yield). ¹H NMR (500 MHz, CDCl₃) δ 6.81 (d, J=9.6 Hz, 1H), 6.61 (d, J=8.3 Hz, 1H), 5.71 (d, J=10.0 Hz, 1H), 5.42 (d, J=10.1 Hz, 1H), 3.06 (t, J=7.1 Hz, 2H), 2.36 (s, 3H), 2.28 (s, 3H); LC/MS 534 (M−H).

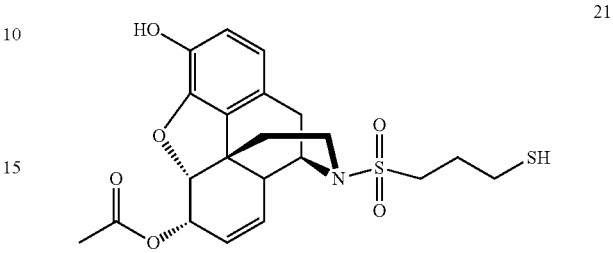

21

Thioacetate 20 (29 mg/0.054 mmol) was dissolved in CH₃OH/THF (2 mL:0.6 mL), followed by the addition of 100 mM sodium phosphate buffer (pH 7.0). 15 mg of hydroxylamine hydrochloride was then added, and the resulting solution was stirred overnight at room temperature. The contents of the vial were transferred to a separatory funnel, EtOAc (10 mL) and water (5 mL) were added, and the funnel was shaken. The layers were separated, and the aqueous layer was extracted with EtOAc (1×5 mL). The combined organic layers were washed with brine (1×5 mL), dried with MgSO₄ and the solvent removed under reduced pressure. The crude product was purified by preparative HPLC to give the pure product as the disulfide derivative of 21 (LC/MS) (2.6 mg/10% yield). Free thiol 21 was obtained by dissolving the disulfide in DMSO:sodium phosphate buffer (pH 7.5) (400 uL DMSO:440 uL 50 mM *NaPi*), followed by the addition of TCEP (2.2 mg/0.008 mmol) in one portion. The resulting solution was stirred at room temperature for 30 minutes to yield 21. LC/MS 452 (M−H).

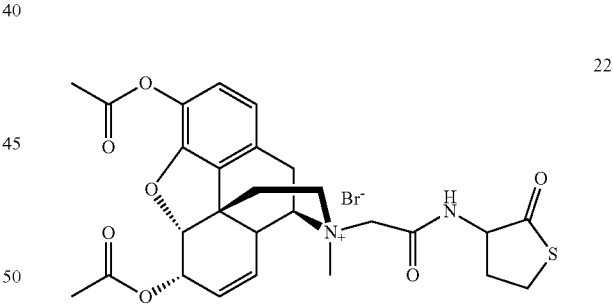

22

Diacetylmorphine 1 (10 mg, 0.03 mmol) was dissolved in acetonitrile (1 mL). To the mixture was added 2-bromo-N-acetyl-HCTL (16 mg, 0.067 mmol). The reaction mixture was then heated at 60° C. for overnight. After overnight, the reaction mixture was cooled down to room temperature. The mixture was then purified using silica TLC plate, eluted with 10% MeOH/DCM to afford 3.6 mg (22%) of 22 as a white powder. ¹H NMR (DMSO-d6) δ 9.14 (1H, d), 6.88 (1H, d), 6.71 (1H, d), 5.65 (1H, d), 5.53 (1H, d); LC/MS 528 (M+).

Example 2. Conjugates

A 6-AM derivative 23 having a linking group containing a sulfhydryl group reactive with maleimide or haloacetyl or haloacetamido moiety:

23

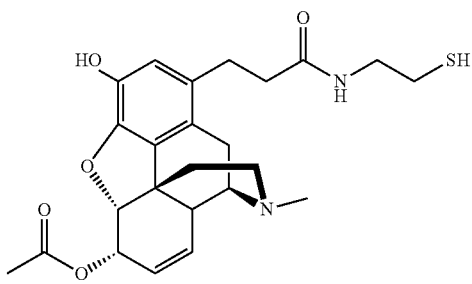

was used to prepare conjugates to a latex solid phase and to KLH as described below.

Bovine serum albumin ("BSA") and polystyrene latex particles (Interfacial Dynamics) were incubated at 25° C. for 30 minutes at 1-10 mg BSA per mL of latex slurry at 1-10% solids in 25 mM citrate buffer, pH approximately 4. The solution was then brought to approximately neutral pH with 150 mM potassium phosphate/30 mM potassium borate, and incubated for an additional 2 hours at 25° C. The suspension was washed three times by resuspension in 50 mM potassium phosphate/10 mM potassium borate/150 mM sodium chloride at approximately neutral pH followed by centrifugation.

An N-hydroxysuccinimide/maleimide bifunctional poly(ethylene glycol) crosslinker as described in U.S. Pat. No. 6,887,952 was added at 5-500 mg/mL in deionized water to the BSA-latex particles at 1-10% solids. The crosslinker was incubated with the BSA-latex particles at room temperature for 2 hours. Excess crosslinker was removed by centrifugation and resuspension in PBS of the now maleimide-functionalized BSA-latex particles.

The derivative (4-8 mg) was dissolved in 0.8 mL DMF-water solution (70:30 v/v) and 200 μL of 1 M KOH, and was incubated for 10 minutes at room temperature. Then the excess of the base was neutralized with a phosphate/hydrochloric acid buffer to pH 7. Maleimide-functionalized BSA-latex particles were added to the solution containing the 6-AM derivative in the presence of 0.1 mM EDTA, and the mixture was incubated at room temperature overnight. KOH was added to maintain the pH at about 7.0. The reaction was stopped in two steps. First by addition of 0.2 mM β-mercaptoethanol and incubation for 30 at room temperature and then by addition of 6 mM N-(hydroxyethyl)maleimide and additional incubation for 30 minutes at room temperature. The 6-AM derivative-conjugated latex particles were purified by centrifugation and resuspension in PBS.

Keyhole Limpet Hemocyanin (KLH, Calbiochem #374817, 50 mg/mL in glycerol) was passed through a 40 mL GH25 column equilibrated in 0.1M potassium phosphate, 0.1M borate, 0.15M sodium chloride buffer, pH 7.5 to remove glycerol. A 1.5-fold molar excess of N-ethylmaleimide was added, and the mixture incubated 30 minutes at room temperature. A 200-fold molar excess of sulfo-SMCC (Pierce #22322) from a 50 mM stock in distilled water was added while vortexing. Vortexing was continued for another 30 seconds, followed by incubation for 10 minutes at room temperature. A 100-fold molar excess of SMCC (Pierce #22360) from an 80 mM stock in acetonitrile was added while vortexing. 1M KOH was added to maintain a pH of between 7.2 and 7.4. The mixture was stirred at room temperature for 90 minutes. After 90 minutes incubation, KLH-SMCC was purified by gel filtration using a GH25 column equilibrated in 0.1M potassium phosphate, 0.02M borate, 0.15M sodium chloride buffer, pH 7.0.

The 6-AM derivative (4-8 mg) was dissolved in 0.8 mL DMF-water solution (70:30 v/v) and 200 μL of 1 M KOH, and was incubated for 10 minutes at room temperature. The excess of the base was neutralized with a phosphate/hydrochloric acid buffer and pH brought to 7. Then, a 2-fold molar excess of derivative (based on the concentration of SMCC in a particular batch of KLH-SMCC) was added to KLH-SMCC, and the mixture stirred for 90 minutes at room temperature. Conjugates were purified by exhaustive dialysis in PBS.

Example 3. Antibodies

Following immunization with the KLH-conjugated derivative, phage display antibody libraries were constructed and enriched using biotin-conjugated 24 and magnetic streptavidin latex as generally described in U.S. Pat. No. 6,057,098. The antibody phage library was selected with 24, transferred into a plasmid expression vector and electroporated into bacterial cells. Simultaneous negative selection was performed with 25, 26, and 27 to select against antibodies binding to undesired epitopes.

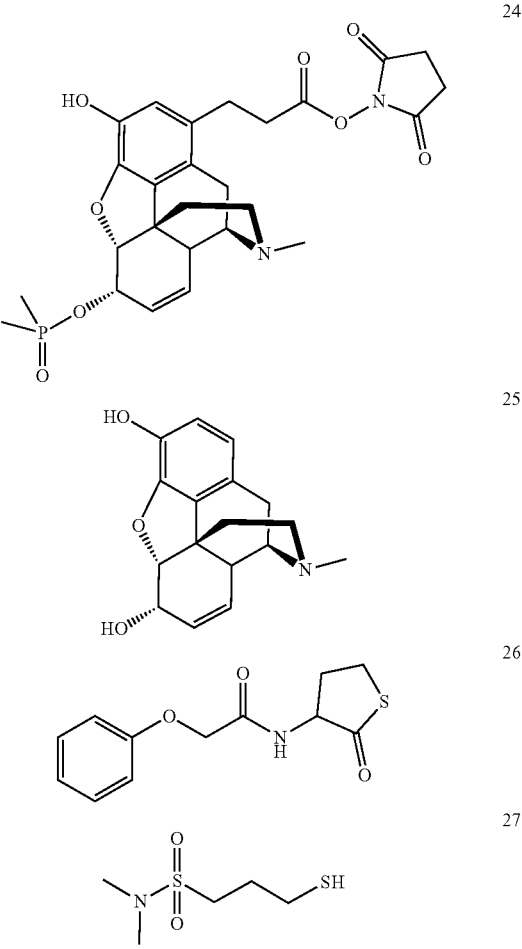

The bacterial cells from each antibody library were streaked on agar to generate colonies. The colonies, coding for monoclonal antibodies, were used to inoculate culture medium in individual wells in 96-well plates. The liquid cultures were grown overnight and used to generate frozen cell stocks. The frozen cell stocks were used to generate duplicate 96-well plate cultures, followed by expression and purification of the monoclonal antibodies in soluble form in microgram quantities. A competitive assay for 6-AM developed with a selected antibody exhibited no crossreactivity with morphine, morphine-3-glucuronide, or morphine-6-glucuronide at clinically relevant concentrations.

Example 4. Cross Reactivity

Cross reactivity to heroin metabolites and other common structurally related opiates were evaluated using the antibodies as described with reference to Example 3. Immunoassays were constructed using the antibodies of Example 3, configured to operate in a competitive mode immunoassay format, in which the analogue compounds of the invention were compared with other related compounds for cross reaction against 6-acetylmorphine. Labeled 6-acetylmorphine conjugates were prepared for use as the detectable species. Aliquots of labeled 6-acetylmorphine at 10 ng/mL were incubated in the presence of competing compound with the antibody of the invention, and the level of interaction of the competitor compound determined as a reduction in measured signal compared with the situation where only 6-acetylmorphine was present. The results are provided in the Table 1. The data demonstrate the high specificity of the antibody for 6-acetylmorphine. With many of the competing species being applied at an excess of 100,000 to 1 over 6-acetylmorphine; there was no detectable cross reaction; and with 6-acetylcodeine at a 30:1 excess over 6-acetylmorphone there was only a 3% cross reaction. The data clearly indicate the specificity of the antibodies of the invention for 6-acetylmorphine.

Figure 7:
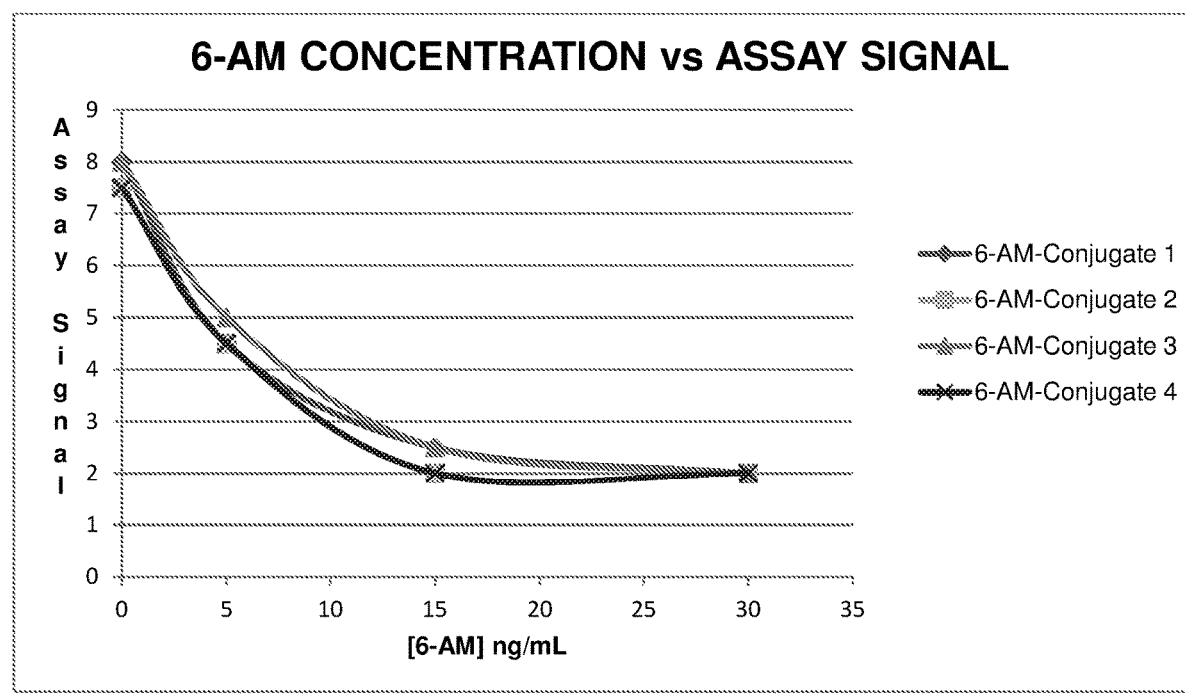
FIG. 7 depicts an assay performance curve generated using multiple lots of 6-AM antigen immunoconjugate against varying concentrations of 6-AM

The data shown in FIG. 7 indicate the behaviors of several 6-actylmorphone conjugates when incubated with the antibody of the invention in the presence of increasing 6-acetylmorphine concentrations, indicating the reduction in signal as the 6-acetylmorphine conjugate is displaced from the antibody by native 6-acetylmorphine.

TABLE 1

| Compound | Analyte Conc. (ng/mL) | 6-AM Conc. (ng/mL) | Cross-Reactivity (%) |
|---|---|---|---|
| 6-Acetylmorphine | 10 | 10 | 100 |
| 6-Acetylcodeine | 300 | 10 | 3 |
| Codeine | 1,000,000 | 10 | Not Detectable |
| Heroin | 750 | 10 | 1.3 |
| Hydrocodone | 1,000,000 | 10 | Not Detectable |
| Hydromorphone | 300,000 | 10 | Not Detectable |
| Morphine | 1,000,000 | 10 | Not Detectable |
| Morphine 3-D-glucuronide | 1,000,000 | 10 | Not Detectable |
| Morphine 6-D-glucuronide | 1,000,000 | 10 | Not Detectable |
| Oxycodone | 1,000,000 | 10 | Not Detectable |
| Oxymorphone | 350,000 | 10 | Not Detectable |

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A compound of formula:

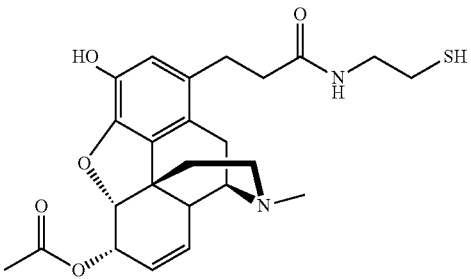

or a salt thereof.

2. A conjugate comprising the compound of claim 1 covalently bound to a protein, polypeptide, detectable label, nucleic acid, or solid phase, wherein the sulfhydryl moiety of the compound is conjugated to a corresponding coupling site on the protein, polypeptide, detectable label, nucleic acid, or solid phase.

3. The conjugate of claim 2, wherein the compound is covalently bound to the detectable label, and the detectable label is selected from the group consisting of an enzyme, a fluorophore, biotin, avidin, streptavidin, digoxigenin, maltose, oligohistidine, 2,4-dinitrobenzene, phenylarsenate, and a fluorescent latex particle.

4. The conjugate of claim 2, wherein the compound is covalently bound to the protein, and the protein is keyhole limpet hem ocyanin or bovine serum albumin.

5. The conjugate of claim 2, wherein the compound is covalently bound to the solid phase, and the solid phase is selected from the group consisting of a membrane, a cellulose-based paper, a polymeric particle, a latex particle, a paramagnetic particle, a glass substrate, a silicon substrate, a plastic substrate, and a multiple-well plate.

6. The conjugate of claim 2, wherein the conjugate further comprises a cross-linker.

7. The conjugate of claim 6, wherein the cross-linker comprises a polyethylene glycol polymer.

8. A method of preparing a conjugate, comprising:
contacting the compound of claim 1 with a protein, polypeptide, detectable label, nucleic acid, or solid phase under conditions selected to provide covalent coupling of said compound to said protein, polypeptide, detectable label, nucleic acid, or solid phase through the sulfhydryl reactive moiety of the compound.

9. The method of claim 8, further comprising introducing said one or more coupling sites corresponding to the sulfhydryl reactive moiety into said protein, polypeptide, detectable label, nucleic acid, or solid phase prior to said contacting step.

10. The method of claim 9, wherein the introducing step comprises coupling of the protein, polypeptide, detectable label, nucleic acid, or solid phase to one or more bivalent crosslinkers.

11. A method of stimulating an immune response to 6-acetylmorphine (6-AM), comprising:
immunizing an animal with a conjugate of claim 4.

12. The method of claim 11, further comprising isolating one or more antibodies that specifically bind 6-AM.

13. The method of claim 12, wherein the one or more antibodies have a binding affinity for 6-AM of at least a factor of 30 greater than the affinity of the antibody for 6-acetylcodeine and heroin, at least a factor of 30,000 greater than the affinity of the antibody for hydromorphone and oxymorphone, and at least a factor of 100,000 greater than the affinity of the antibody for codeine, hydrocodone, morphine, morphine 3-D-glucuronide, morphine 6-D-glucuronide, and oxycodone.

14. The method of claim 12, wherein said one or more antibodies are isolated directly from said animal.

15. A method of determining a 6-acetylmorphine (6-AM) concentration in a sample, comprising:
performing a competitive binding assay using a conjugate according to claim 3 which competes with 6-AM in said sample for binding to an antibody, wherein the conjugate comprises a detectable label covalently bound thereto, wherein a signal obtained from determining an amount of detectable label bound to the antibody in said assay is indicative of the concentration of 6-AM in said sample; and
determining the concentration of 6-AM in said sample from the assay signal.

* * * * *